(12) United States Patent
Kanthasamy et al.

(10) Patent No.: US 9,956,233 B2
(45) Date of Patent: May 1, 2018

(54) NEUROPROTECTION BY MITOCHONDRIA-TARGETED METFORMIN

(71) Applicants: Iowa State University Research Foundation, Inc., Ames, IA (US); The Medical College of Wisconsin, Inc., Milwaukee, WI (US)

(72) Inventors: Anumantha Kanthasamy, Ames, IA (US); Balaraman Kalyanaraman, Wauwatosa, WI (US)

(73) Assignees: Iowa State University Research Foundation, Inc., Ames, IA (US); The Medical College of Wisconsin, Inc., Milwaukee, WI (US)

( * ) Notice: Subject to any disclaimer, the term of this patent is extended or adjusted under 35 U.S.C. 154(b) by 0 days. days.

(21) Appl. No.: 15/294,083

(22) Filed: Oct. 14, 2016

(65) Prior Publication Data

US 2017/0106006 A1    Apr. 20, 2017

Related U.S. Application Data

(60) Provisional application No. 62/241,818, filed on Oct. 15, 2015.

(51) Int. Cl.
*A61K 31/662* (2006.01)
*A61K 31/44* (2006.01)
*A61K 31/4425* (2006.01)

(52) U.S. Cl.
CPC ........ *A61K 31/662* (2013.01); *A61K 31/4425* (2013.01)

(58) Field of Classification Search
CPC ............................ A61K 31/4425; A61K 31/66
See application file for complete search history.

(56) References Cited

FOREIGN PATENT DOCUMENTS

WO    WO2016025725    *   2/2016    ........... A61K 33/155

OTHER PUBLICATIONS

El-Mir et al (J.Mol. Neurosci, (2008) 34:77-87).*
Li et al. (Pharmacology, Biochemistry and Behavior 101 (2012) 564-574.*
Ma et al (Neuroscience letters, 411 (2007) 98-103).*
Patil et al. (Neuroscience, 277 (2014) 747-754).*
Trumbull, Kari A., et al. "Diapocynin and apocynin administration fails to significantly extend survival in G93A SOD1 ALS mice." Neurobiology of disease 45.1 (2012): 137-144.
Jin, Huajun, et al. "Mitochondria-targeted antioxidants for treatment of Parkinson's disease: preclinical and clinical outcomes." Biochimica et Biophysica Acta (BBA)—Molecular Basis of Disease 1842.8 (2014): 1282-1294.
Ghosh, Anamitra, et al. "Neuroprotection by a mitochondria-targeted drug in a Parkinson's disease model." Free Radical Biology and Medicine 49.11 (2010): 1674-1684.

(Continued)

*Primary Examiner* — Savitha M Rao
(74) *Attorney, Agent, or Firm* — Quarles & Brady LLP

(57) ABSTRACT

The present invention provides modified metformin compounds, particularly mito-metformin compounds, and pharmaceutical compositions thereof. Methods of using the compounds to provide neuroprotection and in the treatment and/or prevention of neurodegenerative diseases are also described.

9 Claims, 9 Drawing Sheets
(9 of 9 Drawing Sheet(s) Filed in Color)

Chemical structures of Met and MitoMet.

(56) References Cited

OTHER PUBLICATIONS

Ghosh, Anamitra, et al. "Anti-inflammatory and neuroprotective effects of an orally active apocynin derivative in pre-clinical models of Parkinson's disease." Journal of neuroinflammation 9.1 (2012): 1.

Dranka, Brian P., et al. "Diapocynin prevents early Parkinson's disease symptoms in the leucine-rich repeat kinase 2 (LRRK2 R1441G) transgenic mouse." Neuroscience letters 549 (2013): 57-62.

Dranka, Brian P., et al. "A novel mitochondrially-targeted apocynin derivative prevents hyposmia and loss of motor function in the leucine-rich repeat kinase 2 (LRRK2 R1441G) transgenic mouse model of Parkinson's disease." Neuroscience letters 583 (2014): 159-164.

Chandran, Karunakaran, et al. "Doxorubicin inactivates myocardial cytochrome c oxidase in rats: cardioprotection by Mito-Q." Biophysical Journal 96.4 (2009): 1388-1398.

Anantharam, Vellareddy, et al. "Pharmacological inhibition of neuronal NADPH oxidase protects against 1-methyl-4-phenylpyridinium (MPP+)-induced oxidative stress and apoptosis in mesencephalic dopaminergic neuronal cells." Neurotoxicology 28.5 (2007): 988-997.

* cited by examiner

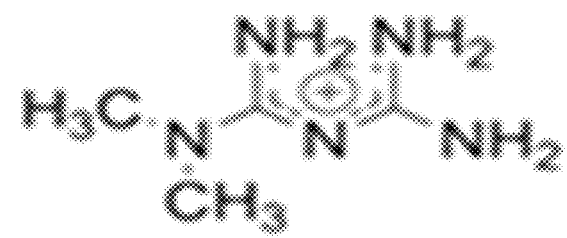
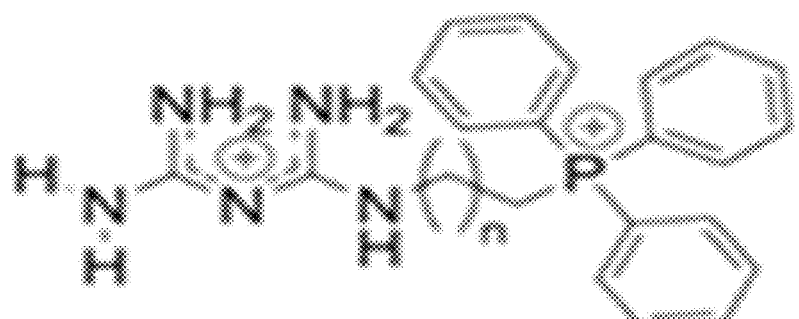
*Chemical structures of Met and MitoMet.*
FIG. 1

Fig 2. Mito-Met (MM) protects against MPP+ and rotenone (Rot)-induced toxicity in N27 dopaminergic neuronal cells. N27 cells were pre-treated with or without 100-300 nM Mito-Met for 1 h and then co-treated with 1 µM rotenone for 3 h (A) or 300 µM MPP+ for 24 h (B). After treatment, Sytox green cytotoxicity (A) and caspase-3 activation (B) were measured.

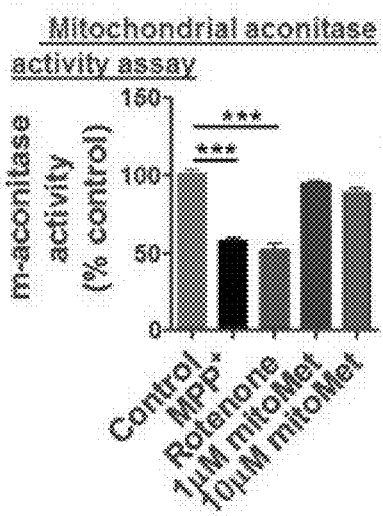
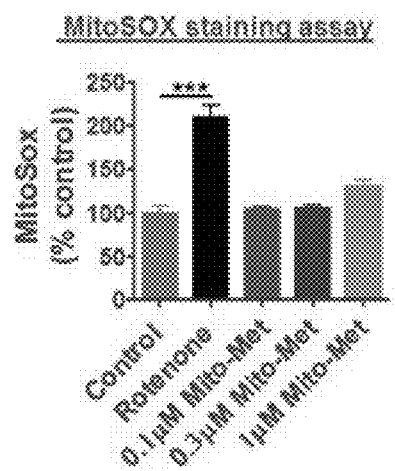
FIG. 3A            FIG. 3B
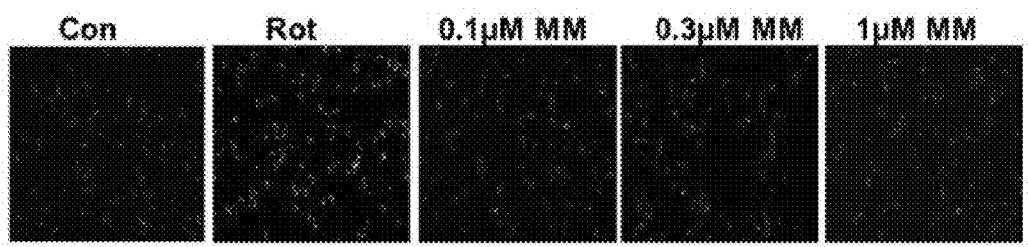
Fig 3. Mito-Met (MM) treatment does not induce mitochondrial oxidative damage in N27 dopaminergic neuronal cells. N27 cells were treated with or without 100-10000 nM Mito-Met for 6 h. After treatment, m-aconitase activity (A) and MitoSox staining (B) assays were performed.
FIG. 3C

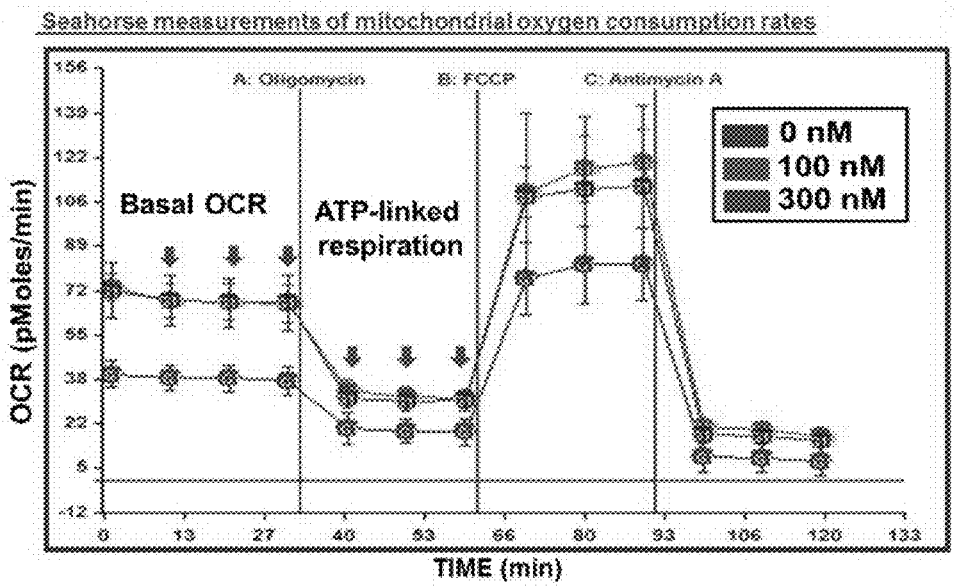
FIG. 4A
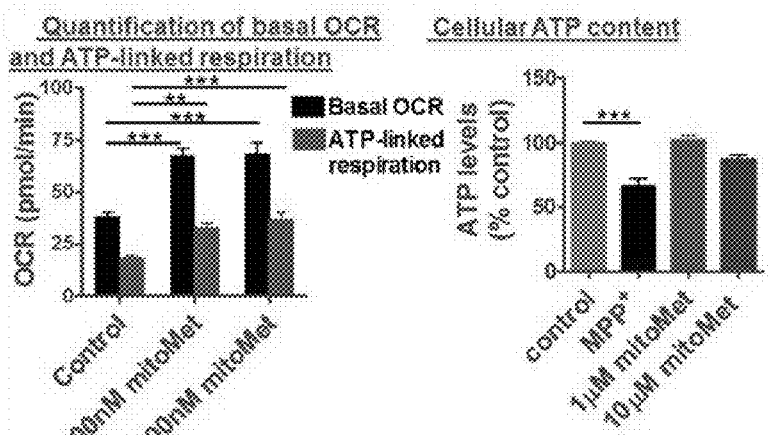
FIG. 4B
FIG. 4C
Fig 4. (A-B) N27 cells were incubated with 100-300 nM Mito-Met for 3 h and assayed for mitochondrial OCR using a Seahorse XF96 extracellular flux analyzer. (C) N27 cells were incubated with 1-10 μM mitoMet for 6 h and assayed for ATP production.

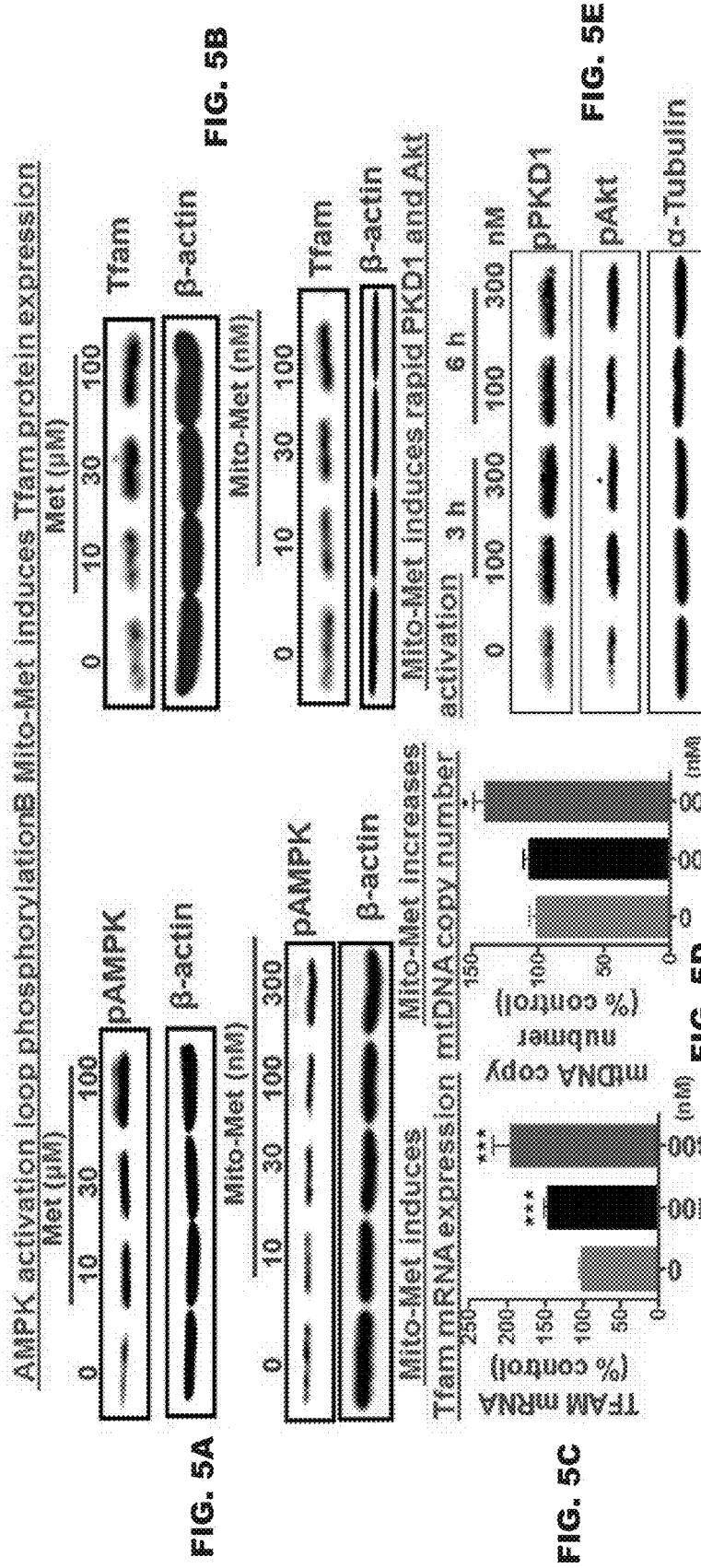

Fig 5. Mito-Met activates AMPK/PKD1/Akt signaling and mitochondrial biogenesis in N27 dopaminergic neuronal cells. (A-B) N27 cells were incubated with or without 10-300 nM Mito-Met or 10-100 μM metformin for 24 h and assayed for AMPK activation (A) and Tfam protein expression (B). (C-E) N27 cells were incubated with or without 100-1000 nM Mito-Met for 3-6 h and assayed for Tfam mRNA expression (C), mtDNA copy number (D) and rapid PKD1 and Akt activation (E).

FIG. 6A
FIG. 6B
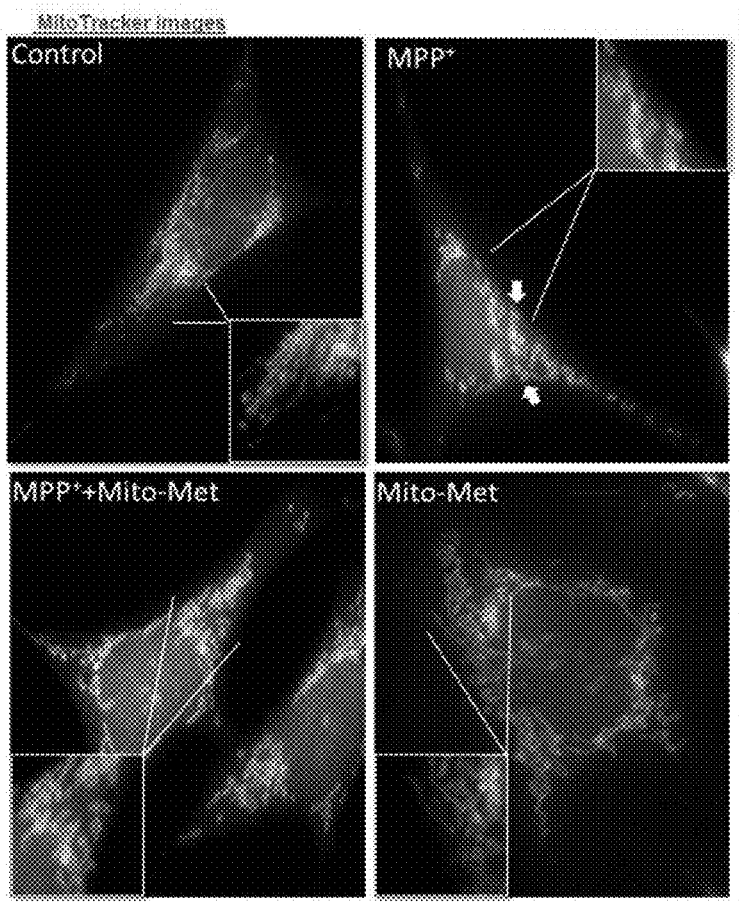
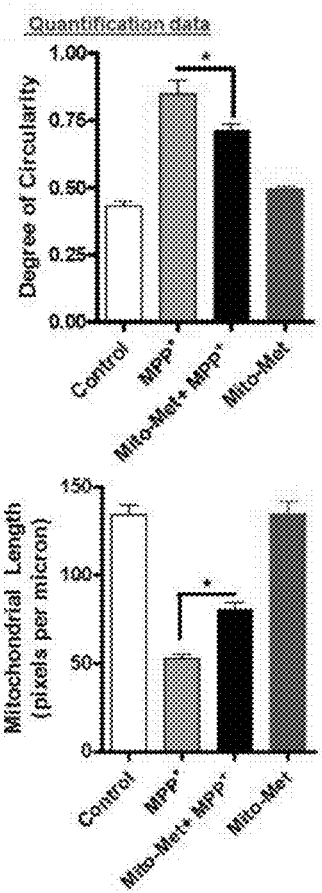
Fig 6. Mito-Met protects MPP+-induced mitochondrial fragmentation. (A) N27 cells were pretreated with 1 µM Mito-Met for 6 h and then co-treated with 300 µM MPP+ for 16 h. Cells were stained with MitoTracker Red. (B) Quantification of mitochondrial length and circularity. Arrow, fragmented mitochondrial.

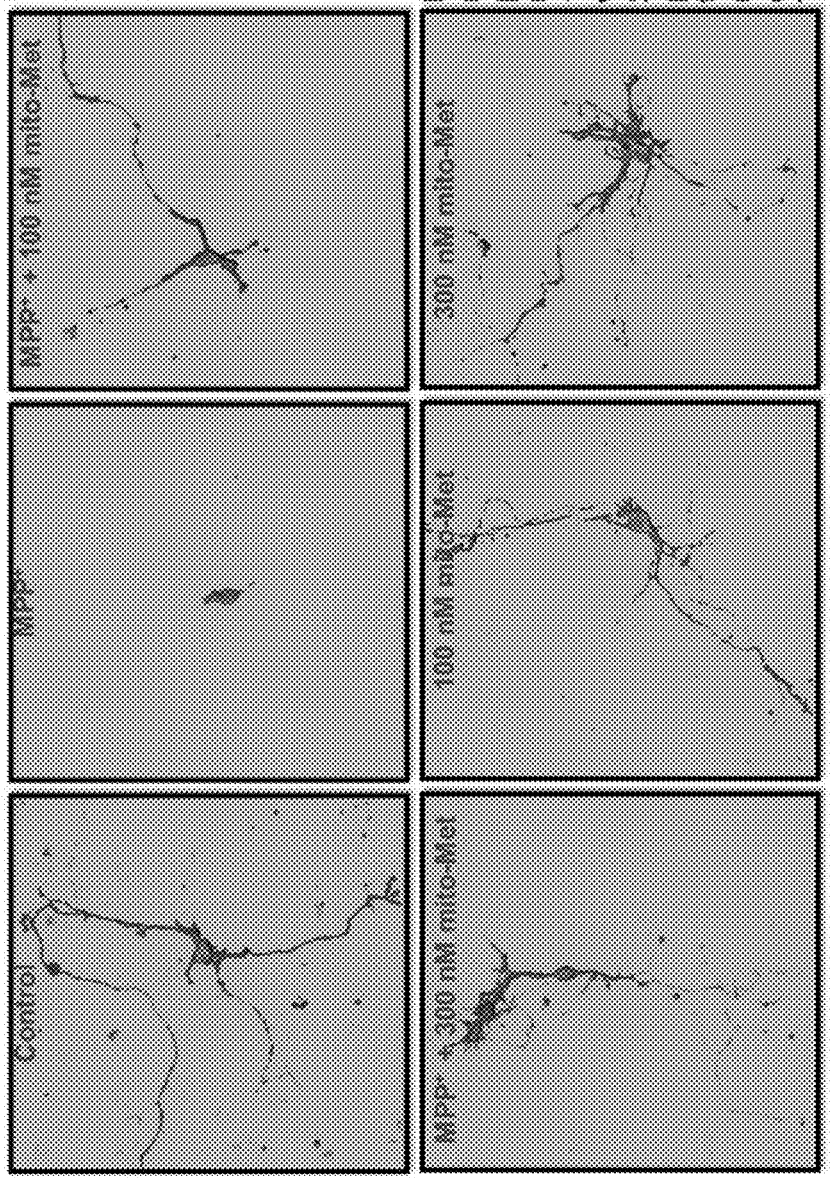
Fig. 7. Mito-Met protects TH+ neurons against MPP+ toxicity in primary neuronal culture. Primary nigral neurons were treated with 10 μM MPP+ alone or co-treated with 100 or 300 nM mito-Met for 24h. (A) TH immunostaining in primary mesencephalic culture from substantia nigra is shown. (B) Cells were subjected to quantification of neurite length of TH+ neurons.

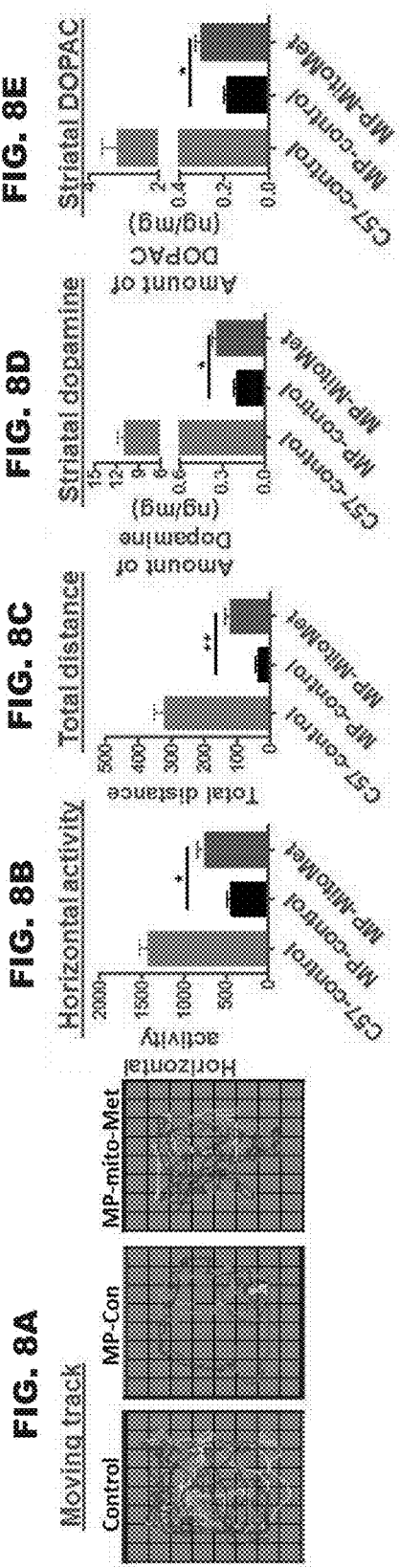

Fig 8. Mito-Met improves locomotor activities and attenuates striatal dopamine depletion in MitoPark mice. 12-week-old MitoPark mice were orally administered with mito-Met (10 mg/kg) three times a week for eight weeks. Control mice received saline. The locomotor activities were measured using a VersaMax analyzer and rotarod one day prior to sacrifice. (A) Moving track of mice; (B) horizontal activity; (C) total distance travelled. One day after the last treatment, mice were sacrificed and dopamine (D) and DOPAC (E) levels were measured from striatum by HPLC.

NEUROPROTECTION BY MITOCHONDRIA-TARGETED METFORMIN

CROSS-REFERENCE TO RELATED APPLICATIONS

This application claims priority to U.S. Provisional Application No. 62/241,818 entitled "Neuroprotection by mitochondria-targeted metformin" filed on Oct. 15, 2016, the contents of which are incorporated by reference in its entirety.

STATEMENT REGARDING FEDERALLY SPONSORED RESEARCH OR DEVELOPMENT

This invention was made with government support under federal grant No. R01 NS039958 awarded by the National Institute of Health (NIH). The government has certain rights in the invention.

FIELD OF THE INVENTION

This invention relates generally to modified metformin compounds, specifically to mito-metformin compounds, and methods of using the modified metformin compounds to provide neuroprotection to a subject. Uses of modified metformin compounds for treatment of neurodegenerative diseases are also disclosed.

BACKGROUND

Mitochondrial diseases represent a clinically heterogeneous group of disorders associated with the dysfunction of the mitochondrial respiratory chain (Kargul et al., 2015; Schapira, 2012). Mitochondrial dysfunction has been established as a pathophysiological hallmark of neurodegenerative diseases, such as Parkinson's, Alzheimer's, Huntington's and Lou Gehrig's Disease. Among these diseases, Parkinson's disease (PD) is the most common aging-related neurodegenerative movement disorder in the United States, with over 630,000 people living with the effects of PD and approximately 60,000 new cases identified each year (Kowal et al. 2013).

The etiology of PD is complex and may involve different genetic and environmental factors that independently or concomitantly contribute to the development of PD (Dardiotis et al. 2013; Schapira and Jenner, 2011; Trinh and Farrer 2013).

Genetic mutations and toxic exposures have both been linked as risk factors in the development of PD>. For example, veterans were subjected to the opportunity for multiple and combined exposures to toxic chemicals, including the herbicides paraquat and Agent Orange (the mixture of two herbicides, 2,4,5-T and 2,4-D) as well as its contaminant TCDD, the organophosphate Malathion, the anti-malaria drug Chloroquine, and the solvent Trichloroethylene (TCE), all of which have been associated with an increased risk of PD (Akahoshi et al., 2009; Bortolozzi et al., 2004; Brighina et al., 2008; Cecil and Young, 2008; Feng, 2006; Hancock et al 2008; Tanner et al., 2011; Young and Cecil 2011; Zaheer and Slevin 2011). An unpublished investigation based on two large population case-control studies of PD by Nelson et al. suggests a significantly increased incidence of PD in veterans who were deployed during either World War II or the Vietnam War (Laino, 2005). Today, approximately 80,000 veterans receiving care and assistance from the Department of Veterans Affairs (VA) are living with PD, and this number does not include those receiving care from other providers. Clinically, this chronic and progressive disease is characterized by resting tremor, rigidity, bradykinesia, postural instability and a broad spectrum of non-motor symptoms, such as autonomic dysfunction, cognitive deficits, depression, and sensory and sleep abnormalities (Ferrer et al., 2012; Sprenger and Poewe, 2013; Taylor et al., 2010). These symptoms ultimately lead to severe disability and reduce quality of life in these elderly patients, imposing a huge economic burden on individuals and society.

According to the Parkinson's Disease Foundation, the combined direct and indirect costs of PD in the United States that include medical expenses, social security payments and reduced employment are estimated at $25 billion per year.

Current treatments are focused mainly on alleviating motor symptoms by compensating for neurochemical deficits, but none of them have been proven to halt or slow disease progression. Therefore, development of better therapeutic agents for treating PD and other similar diseases will have immense implications in the healthcare needs of affected military personnel or civilians. No effective treatment options are available that improve the efficiency of mitochondrial function in these neurodegenerative diseases. Therefore, a need exists for compounds that are effective in inhibiting neuronal cell death and degeneration, or provide neuronal protection.

SUMMARY OF THE INVENTION

The present technology provides methods of providing enhanced neurobehavioral and neuroprotective benefits against mitochondrial defect-linked neurodegenerative processes by administration of modified metformin compounds.

In some aspects, the disclosure provides a method for providing a subject in need thereof with neuroprotection, comprising administering to said subject a neuroprotective composition which includes an effective amount of at least one modified metformin compound.

In another aspect, methods of preventing apoptosis of neuronal cells in a subject are provided. The method comprises administering an effective amount of at least one modified metformin compound.

In further aspects, methods of providing protection of neurons in a subject after neuronal insult are provided. Such methods comprise administering an effective amount of at least one modified metformin compound. In some aspects, the neuronal insult is a result of neurodegenerative disease.

Yet another aspect provides methods for treating neural injury in a subject having a neurodegenerative disease, comprising administering to a subject in need an effective amount of at least one neuroprotective compound, wherein the at least one neuroprotective compound comprises a modified metformin compound.

Further aspects provide a method for treating a neurodegenerative disorder in a subject, comprising administering to a subject in need of such therapy an effective amount of a neuroprotective compound, wherein the neuroprotective compound is a modified metformin compound.

In yet another aspect, the disclosure provides a method of improving mitochondrial function in a subject with a neurodegenerative disease, comprising administering to a subject in need of such treatment an effective amount of a neuroprotective compound, wherein the neuroprotective compound is a modified metformin compound.

In some aspects, the modified metformin is selected from the group consisting of mito-metformin, mito-phenformin, mito-PEG-metformin, mito-cy-metformin or pyrformin. The mito-metformin compound may be in accordance with the following structure:

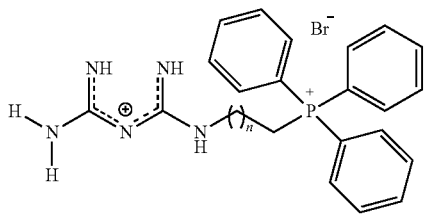

wherein n is a positive integer selected from 1-11.
In some aspects, the mito-metformin compound may be in accordance with the following structure:

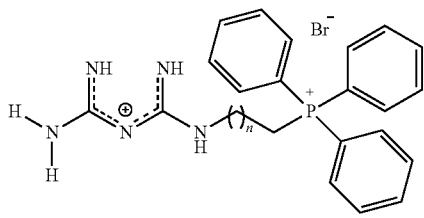

n = 1 - Mito-Metformin-$C_2$
5 - Mito-Metformin-$C_6$
9 - Mito-Metformin-$C_{10}$
11 - Mito-Metformin-$C_{12}$ In yet another aspect, modified metformin compound for the treatment of a neurodegenerative disease are provided, wherein the modified metformin compound is selected from the group consisting of mito-metformin, mito-phenformin, mito-PEG-metformin, mito-cy-metformin or pyrformin.

In another aspect, modified metformin compound for the treatment of neuronal cell death in a patient are provided, wherein the modified metformin compound is selected from the group consisting of a mito-metformin, a mito-phenformin, a mito-PEG-metformin, a mito-cy-metformin or a pyrformin.

In a further aspect, a neuroprotective composition for providing neuroprotection in a subject suffering from a neurodegenerative disease is provided, where the composition comprises at least one modified metformin compound.

In yet another aspect, a method of preventing, reducing or treating at least one symptom of a neurodegenerative disease is provided comprising administering a neuroprotective composition comprising at least one modified metformin compounds in an amount effective to prevent, reduce or treat at least one symptom of the neurodegenerative disease.

Other features of the present invention will become apparent after review of the specification, claims and drawings.

BRIEF DESCRIPTION OF THE DRAWINGS

This patent application file contains at least one drawing executed in color. Copies of this patent or patent application publication with color drawing(s) will be provided by the Office upon request and payment of the necessary fee.

FIG. 1 depicts the structure of Metformin and Mito-Metformin (Mito-Met).

FIG. 3A-C depicts that Mito-Met treatment does not induce mitochondrial oxidative damage in N27 dopaminergic neuronal cells. N27 cells were treated with or without 100-10000 nM Mito-Met for 6 hours. After treatment, m-aconitase activity (FIG. 3A) and MitoSox staining (FIG. 3B) were performed. The representative figures of the MitoSox staining are shown in FIG. 3C.

FIG. 4A-C depicts Mito-Met effect on mitochondrial oxygen consumption rates (OCR). Line graph (FIG. 4A) and bar graph (FIG. 4B) show that N27 cells were incubated with 100-300 nM Mito-Met for 3 hour and assayed for mitochondrial OCR using a Seahorse XF96 extracellular flux analyzer (A-B). Bar graph (FIG. 4C) depicts N27 cells incubated with 1-10 µM mito-Met for 6 h and assayed for ATP production. N27 cells.

FIG. 5A-E depicts the activation of AMPK/PKD1/Akt signaling and mitochondrial biogenesis in N27 dopaminergic neuronal cells. FIG. 5A-B show N27 cells were incubated with or without 10-300 nM Mito-Met or 10-100 µM metformin for 24 h and assayed for AMPK activation (FIG. 5A) and TFAM protein expression (FIG. 5B). FIG. 5C-E depict N27 cells that were incubated with or without 100-1000 nM Mito-Met for 3-6 h and assayed for Tfam mRNA expression (FIG. 5C), mtDNA copy number (FIG. 5D) and rapid PKD1 and Akt activation (FIG. 5E).

FIG. 6A-B depict Mito-Met protection of cells against MPP+-induced mitochondrial fragmentation. FIG. 6A shows pictures of N27 cells that were pretreated with 1 µM Mito-Met for 6 h and then co-treated with 300 µM MPP+ for 16 h. Cells were stained with MitoTracker Red. Arrows depict fragmented mitochondrial. FIG. 6B graphically demonstrates quantification of mitochondrial length and circularity.

FIG. 7A-B shows Mito-Met protection of TH+ neurons against MPP+ toxicity in primary neuronal culture. Primary migral neurons were treated with 10 µM MPP+ alone or co-treated with 100-300 nM mito-Met for 24 h. FIG. 7A shows TH immunostaining in primary mesencephalic culture from substantia nigra. FIG. 7B depicts quantification of neurite length of TH+ neurons.

FIG. 8A-E depicts Mito-Met improvement of locomotor activities and ability to attenuate striatal dopamine depletion in MitoPark mice. 12-week-old MitoPark mice were orally administered with mito-Met (10 mg/kg) three times a week for eight weeks. Control mice received saline. The locomotor activities were measured using a VersaMax analyzer and rotarod one day prior to sacrifice. FIG. 8A depicts moving track of mice. FIG. 8B depicts horizontal activity. FIG. 8C depicts total distance travelled. One day after the last treatment, mice were sacrificed and dopamine (FIG. 8D) and DOPAC (FIG. 8E) levels were measured from striatum by HPLC.

DETAILED DESCRIPTION OF THE INVENTION

Figure 2A:
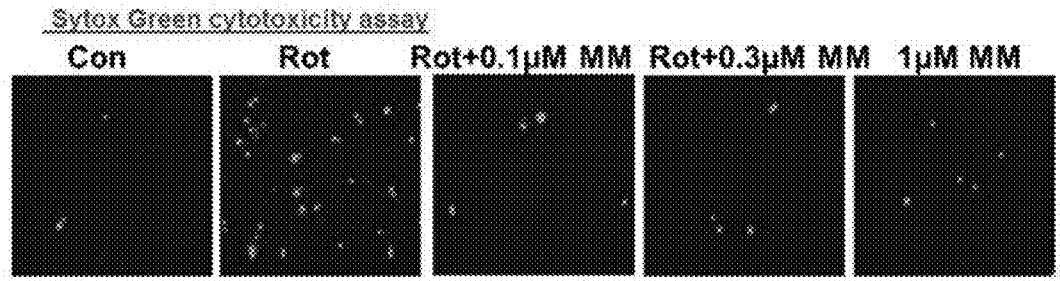
FIG. 2A-B depicts the ability of Mito-Met (MM) to protect against MPP+ and rotenone (Rot)-induced toxicity in N27 dopaminergic neuronal cells. N27 cells were pretreated with or without 100-300 nM Mito-Met for 1 hour and then co-treated with 1 µM rotenone for 3 h or 300 µM MPP+ for 24 h. After treatment, Syntox green cytotoxicity was visualized by microscopy and plotted as a percent control (FIG. 2A) and caspase-3 activation (FIG. 2B) was measured.

In General.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

The present technology provides novel mito-metformin (Mito-Met) compounds that provide neuroprotection and neuro-restorative properties when targeted for specific uptake in mitochondria of cells. Specifically, the inventors have shown that attaching a positively-charged group to metformin greatly enhances the compounds ability to increase mitochondrial sequestration and increase bioavailability in the brain of a subject. The mito-met compounds have increased brain penetrant properties. Further, the modified metformin provide enhanced neuroprotection against dopaminergic neurodegeneration. These neuroprotective compounds may be used to prevent, treat or reduce symptoms in a subject suffering from neurodegenerative disease. These compounds also increase bio-energetic-sensing mechanisms including AMPK-PKD1 survival signaling leading to enhanced mitochondrial biogenesis in neuronal cells. Further, it was found that in nanomolar concentrations of mito-Met itself did not inhibit, but rather improved mitochondrial oxygen consumption rate in dopaminergic cells.

Metformin, a biguanide from *Galega officinalis*, is an FDA-approved drug for treating diabetes, which inhibits hepatic gluconeogenesis. Metformin exists as a hydrophilic cation at physiological pH and targets mitochondria, albeit rather inefficiently. Metformin has been in use in the clinic for over 50 years and has a very good safety profile (diabetic patients tolerate daily doses of 2-3 grams).

This disclosure demonstrates that a novel, mitochondria-targeted metformin analogs (Mito-Met) have increased uptake in mitochondria of cells and provide neuroprotective and neuro-restorative benefits to subjects. These modified metformin can be used to prevent, treat or alleviate symptoms of neurodegenerative disease.

The reasons for apoptotic death of dopaminergic (dopamine producing) neuronal cells in neurodegenerative diseases are not known. Proposed mechanism include genetic mutation, chronic inflammation, or exposure to environmental toxins. It is hypothesized that activation of resident immune cells in the brain by inflammatory mediators contributes to the death or degeneration of neurons.

The neuropathology of PD mainly includes degeneration of dopaminergic neurons in the substantia nigra (SN) and accumulation of misfolded αSyn into the cytoplasmic inclusions called Lewy bodies and Lewy neurites (Chen et al., 2008; Hakansson et al 2005; Hirsch and Hunot 2009; Kruger et al., 2000; McGeer et al., 2002; Przedborski, 2010; Schwab et al., 2010; Wahner et al., 2007; Wu et al., 2007; Yan et al., 2014). Currently, the precise pathogenesis of PD remains incompletely understood, but substantial evidence from both experimental models and postmortem human brain tissues indicates that mitochondrial dysfunction and oxidative stress play a central role in the pathogenesis of this disease (Beal, 2003; Chaturvedi and Flint Beal, 2013; Exner et al. 2012; Keogh and Chinnery, 2015; Lopert et al 2012; Moon and Paek, 2015; Ryan et al., 2015; Sanders and Greenamyre, 2013; Subramaniam and Chesselet, 2013). A major mechanism implicated in the mitochondrial dysfunction seen in PD models is impaired mitochondrial biogenesis, a process heavily depending on coordinated transcriptional control of genes encoding for mitochondrial proteins through the PGC-1α-NRF1/2-Tfam transcriptional cascade (Dominy and Puigserver, 2013; Scarpulla et al., 2012; Valero, 2014; Villena, 2015). The transcriptional coactivator PGC-1α is a master regulator of mitochondrial biogenesis and cellular energy metabolism. A large-scale genome-wide expression meta-analysis study has revealed that PGC-1α-responsive genes, which regulate cellular bioenergetics, are specifically down-regulated in early PD patients (Zheng et al., 2010), further highlighting protective role of PGC-1α in PD. Additional studies revealed a reduced expression of many mitochondrial biogenesis factors in brain tissues of PD patients (Thomas et al., 2012). Importantly, PGC-1α activation has been shown to be neuroprotective against dopaminergic degeneration in cell culture and animal models of PD (Mudo et al., 2012; O'Donnell et al., 2014; Shin et al., 2011; Zheng et al., 2010. Thus, the strategies to upregulate PGC-1α has recently been recognized as a viable option to improve mitochondrial defects in PD (Ciron et al. 2015; Pacelli et al. 2011; Tsunemi and La Spada, 2012).

Mechanistically, PGC-1α can be activated by its upstream regulators, such as AMP-activated kinase (AMPK), which consisting of a catalytic α-subunit, regulatory β-subunit, and an AMP/ATP-binding γ-subunit directly phosphorylates and activates PGC-1α (Jager et al., 2007; Roman et al. 2010). Activation of AMPK pathway has emerged as an important intracellular mechanism of neuroprotection neurological disease including PD (Choi et al., 2010 Grahame Hardie, 2014; Ng et al., 2012; Steinberg and Kemp, 2009).

The inventors have discovered that brain PKD1 signaling represents a novel compensatory protective mechanism in PD models (Asaithambi et al., 2014; Asaithambi et al, 2011; Ay et al., 2015) and can possibly regulate mitochondrial biogenesis. As demonstrated in the Examples, the inventors demonstrate that PKD1 is an upstream regulator of AMPK and PGC-1α signaling, which is integral for mitochondrial biogenesis. Thus, the inventors reason that drugs that active PKD1 can promote mitochondrial biogenesis through AMPK and PGC-1α activation and thereby will afford neuroprotection for PD. Modified metformin described herein is shown to increase activation of PKD1 pro-survival signaling. Thus, not to be bound by any theory, but in some embodiments, neurons are rescued from apoptotic cell death by the addition of pro-survival signaling induced by treatment with the modified metformin compounds described herein.

Neuroprotective compounds of the present technology may be used to inhibit, reduce, delay or mitigate neurodegeneration in a subject, which, in turn may postpone the onset or lessen the effects of neurodegenerative diseases. Neurodegenerative diseases are associated with symptoms of reduced motor ability and cognition. For example, symptoms of Parkinson's disease include, but are not limited to, loss of motor control, tremors at rest, bradykinesia (slowness of movement), rigidity and stiffness, postural instability (impaired balance) and a broad spectrum of non-motor symptoms, such as autonomic dysfunction, cognitive deficits, depression, and sensory and sleep abnormalities (Ferrer et al., 2012; Sprenger and Poewe, 2013; Taylor et al., 2010). Neurodegradation may also be measured on cellular level, for example, abnormal protein aggregation, mitochondrial oxidative damage, decreased mitochondrial biogenesis, reduced cellular ATP production, increased apoptotic cell death, and others. Thus, compounds described herein may alleviate one or more of the cellular damage or symptoms associated with neurodegenerative diseases.

Specifically, the inventors have shown that mitochondria-targeted metformin analogs (Mito-Mets) are significantly more potent than metformin in enhancing mitochondrial oxygen consumption, AMPK activation, PKD-1 signaling and mitochondrial biogenesis. The Examples herein show that mito-Met at nM concentrations activate PKD1, AMPKα1 and PGC-1α signaling in dopaminergic neuronal cell model, demonstrating the enhanced mitochondrial biogenesis capacity when compared to Met alone.

As Met targets mitochondria, although not very effectively, the addition of a positively-charged lipophilic substituent has enhanced the mitochondria uptake of the compound and resulted in a surprisingly increased enhancement of neuroprotection. Suitable neuroprotective compositions includes Mito-Met analogs conjugated to varying alkyl chain lengths containing a triphenylphosphonium cation (TPP+).

Results show that Mito-Met analogs synthesized by attaching TPP+ to Met via a carbon aliphatic side chain is able to protect dopaminergic neuronal cells against apoptotic cell death (as measured by caspase-3 activity) induced by Parkinsonian mitochondrial toxicant MPP+ and does not provide any adverse side effects. Further, Mito-Met analogs did not result in attenuated activity of mitochondrial aconitase, whose inactivation is commonly used as a measure of mitochondrial oxidative damage.

The neuroprotective compounds used in the methods described herein can be one or more modified metformin that has increased uptake and targeting to mitochondria. In some embodiments, the neuroprotective compounds are one or more mito-metformin compounds described herein.

Modified mitochondrial-metformin (Mito-Met) for use in the present technology are disclosed in PCT Application No. PCT/US2015/045075 filed on Aug. 13, 2015 entitled "Compounds and Methods of Synthesis and Uses Thereof," the contents of which are incorporated by reference in its entirety.

In one embodiment, the mito-metformin compounds used in the methods and uses of the present technology are of the following structure:

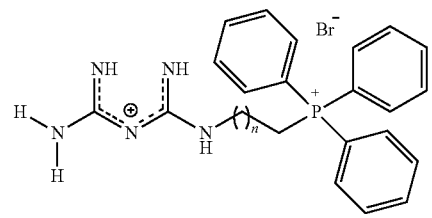

wherein n is a positive integer from 1-11. In some embodiments, n is selected from the group consisting of one (n=1, Mito-Metformin-C$_2$), five (n=5, Mito-Metformin-C$_6$), nine (n=6, Mito-Metformin-C$_{10}$), and eleven (n=11, Mito-Metformin-C$_{12}$).

In one embodiment, the mito-met compounds used in the methods and uses of the present technology are as follows:

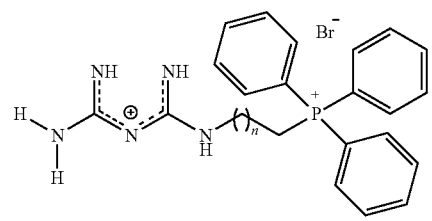

n = 1 - Mito-Metformin-C$_2$
    5 - Mito-Metformin-C$_6$
    9 - Mito-Metformin-C$_{10}$
    11 - Mito-Metformin-C$_{12}$ In another embodiment, the mito-met compound used in the methods and uses of the present technology comprises the following structure:

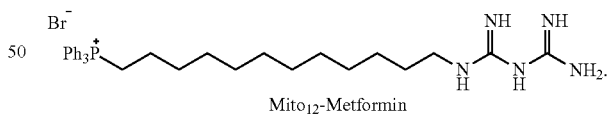

Mito$_{12}$-Metformin

In another embodiment, the mito-met compound used in the methods and uses of the present technology comprises the following structure:

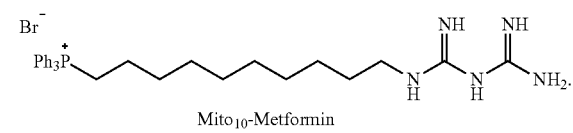

Mito$_{10}$-Metformin

In yet another embodiment, the mito-met compound used in the methods and uses of the present technology comprises the following structure:

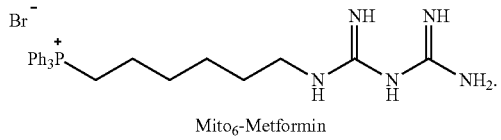

Mito₆-Metformin

In a further embodiment, the mito-met compound used in the methods and uses of the present technology comprises the following structure:

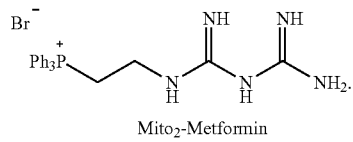

Mito₂-Metformin

In another embodiment, the mito-met compound used in the methods and uses of the present technology comprises the following structure:

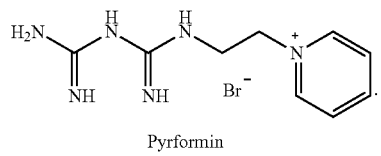 [SMILES: N=C(N)NC(=N)NCC[n+]1ccccc1 ; [Br-]]

Pyrformin

In another embodiment, the mito-met compound used in the methods and uses of the present technology comprises the following structure:

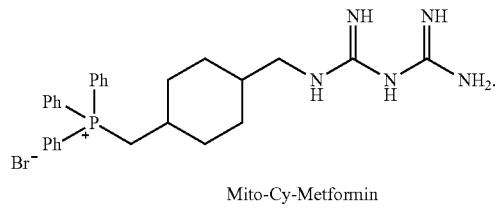 [SMILES: N=C(N)NC(=N)NCC1CCC(C[P+](c2ccccc2)(c2ccccc2)c2ccccc2)CC1 ; [Br-]]

Mito-Cy-Metformin

In yet another embodiment, the mito-met compound used in the methods and uses of the present technology comprises the following structure:

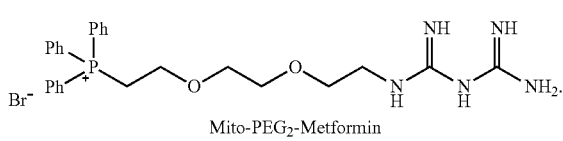

Mito-PEG₂-Metformin

In another embodiment, the mito-met compound used in the methods and uses of the present technology comprises the following structure:

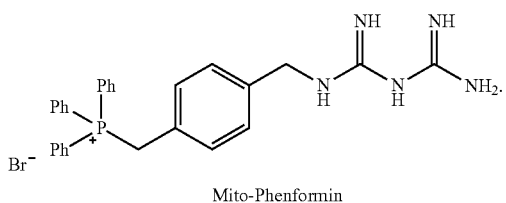 [SMILES: N=C(N)NC(=N)NCc1ccc(C[P+](c2ccccc2)(c2ccccc2)c2ccccc2)cc1 ; [Br-]]

Mito-Phenformin

In another embodiment, the mito-met compound used in the methods and uses of the present technology comprises the following structure:

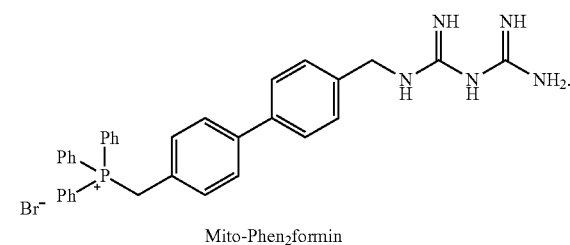 [SMILES: N=C(N)NC(=N)NCc1ccc(-c2ccc(C[P+](c3ccccc3)(c3ccccc3)c3ccccc3)cc2)cc1 ; [Br-]]

Mito-Phen₂formin

In some embodiments, the composition may contain, one, at least one or a combination of one or more mito-met compounds of the present technology. In some embodiments, the composition may contain, one, two, three, four, etc. mito-met compounds.

The disclosure provides neuroprotective compositions for providing neuroprotection in a subject suffering from a neurodegenerative disease comprising at least one modified metformin compound. In some embodiments, the modified metformin is Mito-Met. The disclosure also provides one or more modified metformin compounds for use in the treatment of a neurodegenerative disease. In other embodiments one or more modified metformin compounds are used to reduce, inhibit, reverse, or delay neuronal cell death in a subject.

Methods of Use.

The disclosure provides a method of providing neuroprotection in a subject comprising administering to the subject a therapeutically effective amount of a neuroprotective composition comprising at least one mito-met compound of the present technology. The composition comprises one mito-met compound, but in alternate embodiments multiple mito-met compounds may be administered.

Some embodiments also provides therapeutic compositions comprising at least one of the mito-met compounds and a pharmacologically acceptable excipient or carrier. The therapeutic composition may advantageously be soluble in an aqueous solution at a physiologically acceptable pH.

In some embodiments, the disclosure provides methods of preventing, reducing, or reversing neuronal cell death or apoptosis in a subject comprising administering a therapeutically effective amount of at least one modified metformin compound as disclosed herein. In some embodiments, the neuronal cell death is caused by a neurodegenerative disease to the subject.

In other embodiments, the disclosure provides methods of protecting neurons in a subject from neuronal insult comprising administering an effective amount of at least one modified metformin compound to the subject. Neuronal insult may be caused by a neurodegenerative disease. In some cases, other diseases or disorders may lead to neurodegeneration.

The disclosure also provides methods of treating neural injury in a subject comprising administering an effective amount of a neuroprotective compound of the present technology. In some embodiments, the neural injury is associated with a neurodegenerative disease, such as Parkinson's disease. Methods for treating a neurodegenerative disorder are provided by administering an effective amount of a neuroprotective compound disclosed herein.

Further embodiments provide methods of improving mitochondrial function in neurons of a subject comprising administering an effective amount of the neuroprotective compounds disclosed herein.

In some embodiments, methods to prolong motor function in subjects with neurodegenerative diseases are provided by administering a therapeutically effective amount of a neuroprotective compounds comprises at least one modified metformin. In some embodiments, prolonged motor function permits the animals to maintain normal or near normal functions for longer periods of time compared to convention therapies.

In some embodiments, the neuroprotective compounds of the present technology may mitigate the effects of neurodegenerative diseases, including, for example, mitochondrial oxidative and nitrosative damage in the brain, enhance and/or prevent decreases in or deficits in neurotransmitter levels, such as, for example, neuronal dopamine levels, prevent microglial and astroglial activation and inhibit cytokine release in the brain. In some cases, the neuroprotective compounds are able to increase dopamine in the brain of a mammal.

In other embodiments, the mito-met compounds of the present invention can, when combined with conventional treatment protocols, increase the effectiveness of conventional treatments.

By "neurodegenerative disease" we mean any disease resulting from neurodegenerative processes, including, for example, amyotrophic lateral sclerosis, Parkinson's, Alzheimer's, and Huntington's Disease.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder.

By "ameliorate." "amelioration," "improvement," "restore," "restorative" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-met compounds of the present invention, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-met compounds of the present invention is administered to a subject or is used in an assay or other method described herein or a cited reference, e.g., within about 1 hour of the administration or use of the mito-met compounds of the present invention to about 3, 6, 9 months or more after a subject(s) has received the mito-met compounds of the present invention.

By "reduce," "inhibit," "reversal" or the like we mean a detectable reduction or a detectable change consistent with reduced neurological symptom or increased motor skills and/or control occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-met compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self-assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-met compounds of the present invention is administered to a subject or is used in an assay or other method described herein or a cited reference, e.g., within about 1 hour of the administration or use of the mito-met compounds of the present invention to about 3, 6, 9 months or more after a subject(s) has received the mito-met compounds of the present invention.

By "administering" we mean any means for introducing the mito-met compounds into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "therapeutically effective amount" we mean an amount effective, at dosages and for periods of time necessary, to achieve the desired therapeutic result. For example, in some embodiments, a therapeutically effective amounts is an amount effective to cause reduction, inhibition, delay or reversal of neurodegeneration in a subject.

In some embodiments, the neurodegeneration is caused by at least one of the following, a neurodegenerative disease, such as Parkinson's disease, Alzheimer's disease, Huntington's disease, amyotrophic lateral sclerosis, or by other disease.

In one embodiment, the therapeutically effective amount ranges from between about 5-500 mg/kg, alternatively 50-300 mg/kg. A therapeutically effective amount of the mito-met compounds may vary according to factors such as the disease state, age, sex, and weight of the subject, and the ability of the mito-met compounds to elicit a desired response in the subject. Dosage regimens may be adjusted to provide the optimum therapeutic response. A therapeutically effective amount is also one in which any toxic or detrimental effects of the mito-met compounds of the present invention are outweighed by the therapeutically beneficial effects.

A "prophylactically effective amount" refers to an amount effective, at dosages and for periods of time necessary, to achieve the desired prophylactic result, such as preventing or inhibiting the rate of neurodegeneration of neurons. A prophylactically effective amount can be determined as described above for the therapeutically effective amount. Typically, since a prophylactic dose is used in subjects prior to or at an earlier stage of disease, the prophylactically effective amount may be, in some cases, less than the therapeutically effective amount.

Kits.

In another embodiment, the present invention provides a kit comprising a pharmaceutical composition comprising the mito-met compounds of the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1. Synthesis of Pyrformin Compounds

The pyrformin compounds of the present invention are synthesized according to the following reaction:

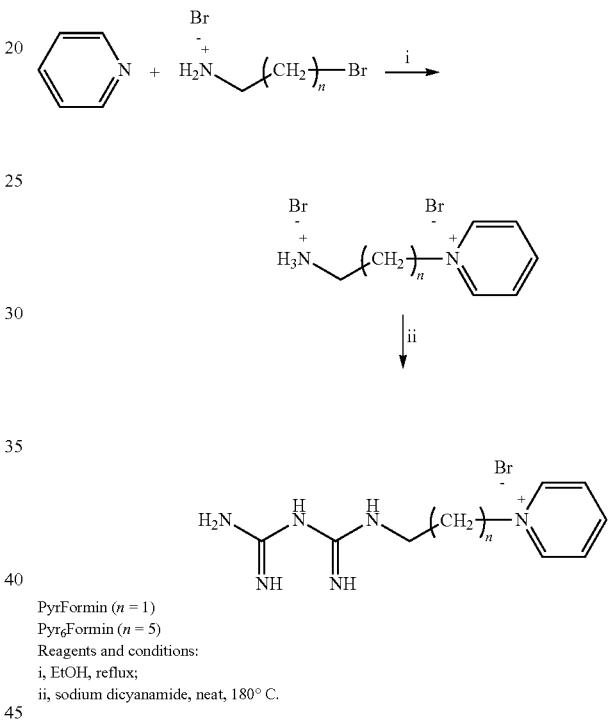

PyrFormin ($n = 1$)
Pyr$_6$Formin ($n = 5$)
Reagents and conditions:
i, EtOH, reflux;
ii, sodium dicyanamide, neat, 180° C.

Example 2. Synthesis of Mito-cy-Metformin Compounds

The Mito-cy-Metformin compounds of the present invention are synthesized according to the following reaction:

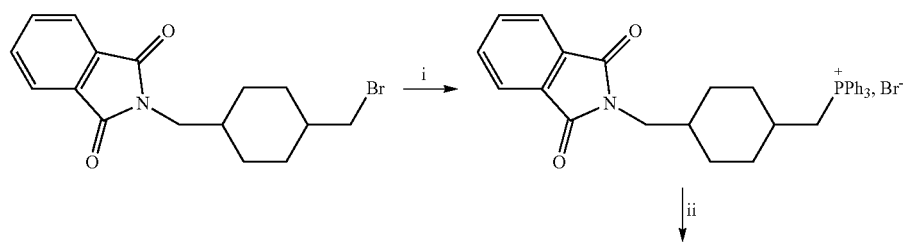

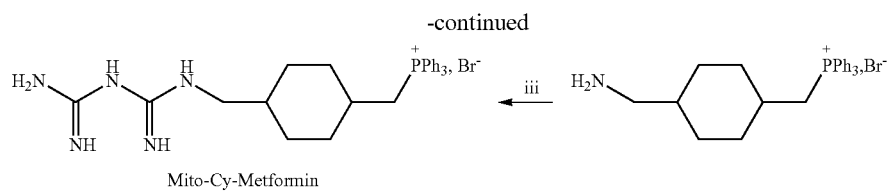

Mito-Cy-Metformin

Reagents and conditions:
i   PPh₃, ACN, reflux,
ii; NH₂—NH₂, EtOH, reflux;
iii, HCl, sodium dicyanamide, neat, 180° C.

Example 3. Synthesis of Mito-PEG-Metformin Compounds

The Mito-PEG-Metformin compounds of the present invention are synthesized according to the following reaction:

Scheme.

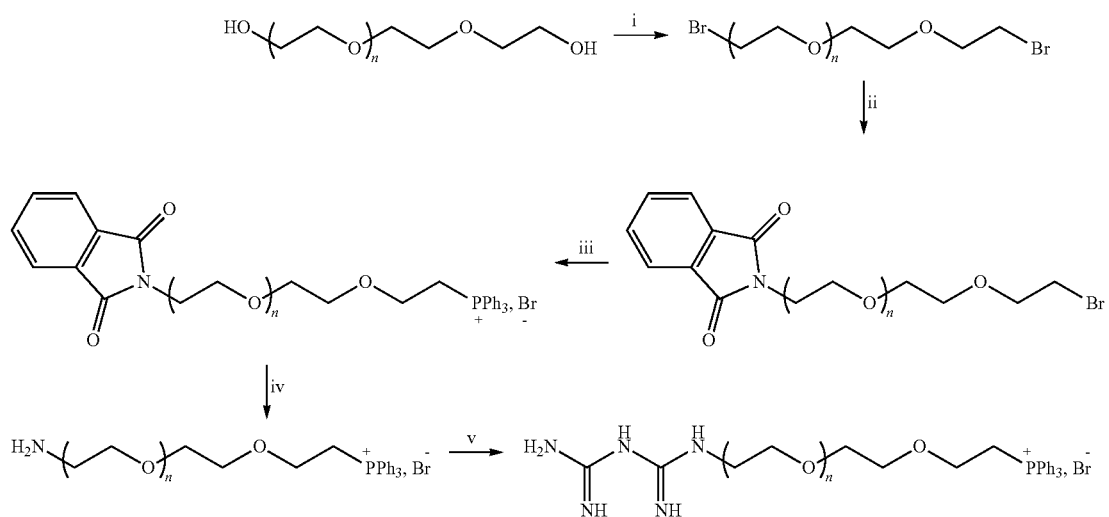

Mito-PEG₂-Metformin (n = 1)
Mito-PEG₃-Metformin (n = 2)
Reagents and conditions:
i, PBr₃;
ii, Potassium phtalimide, DMF;
iii, PPh₃, ACN, reflux;
iv, NH₂—NH₂, EtOH, reflux;
v, HCl, sodium dicyanamide, neat, 180° C.

Example 4. Synthesis of Mito-Phenformin Compounds

The Mito-Phenformin compounds of the present invention are synthesized according to the following reaction:

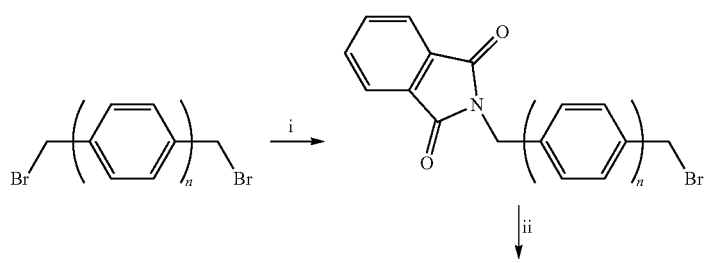

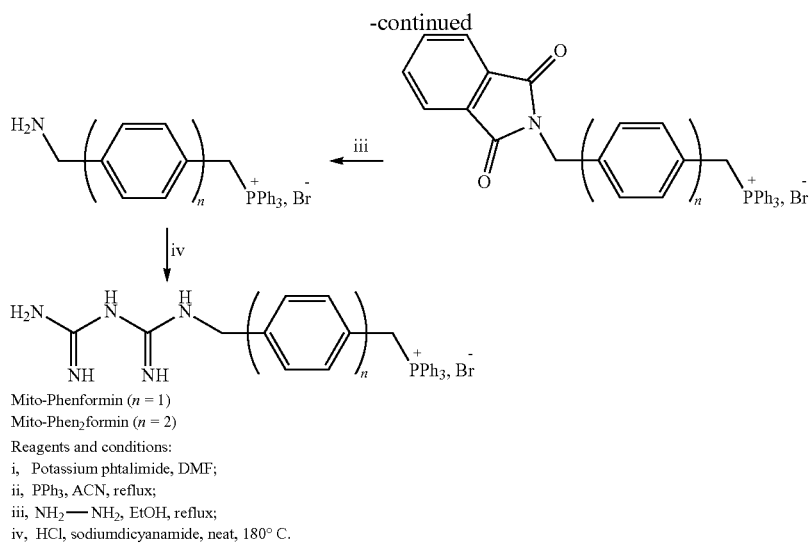

Mito-Phenformin (*n* = 1)
Mito-Phen₂formin (*n* = 2)
Reagents and conditions:
i, Potassium phtalimide, DMF;
ii, PPh₃, ACN, reflux;
iii, NH₂—NH₂, EtOH, reflux;
iv, HCl, sodiumdicyanamide, neat, 180° C.

Example 5. Synthesis of Mito-Metformin Compounds

The mito-metformin compounds of the present invention were synthesized according to the following reaction:

Scheme.

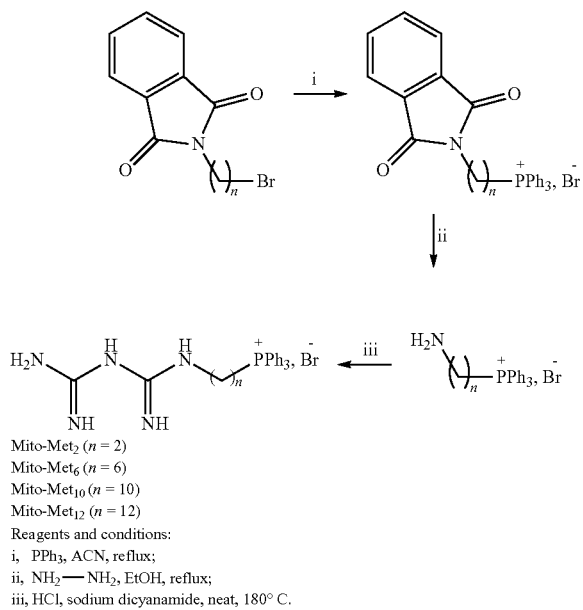

Mito-Met₂ (*n* = 2)
Mito-Met₆ (*n* = 6)
Mito-Met₁₀ (*n* = 10)
Mito-Met₁₂ (*n* = 12)
Reagents and conditions:
i, PPh₃, ACN, reflux;
ii, NH₂—NH₂, EtOH, reflux;
iii, HCl, sodium dicyanamide, neat, 180° C.

Example 6. Synthesis of Mito₂-Metformin (Mito-Met₂) 1

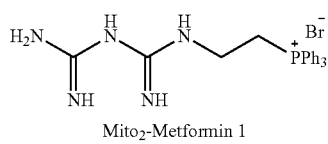

Mito₂-Metformin 1

A 0.1 g portion of (2-Aminoethyl) triphenylphosphonium Bromide (0.26 mmol) was dissolved in $CH_2Cl_2$ (3 mL) and the mixture was cooled to 0° C. A 336 μL portion of 1.0 M solution of HCl in diethyl ether (0.33 mmol) was added dropwise. After 1 h 30 at room temperature, the solvent was removed under vacuum. Sodium dicyanamide (0.026 g, 0.31 mmol) was added in BuOH (3 mL). The mixture was heated to reflux overnight, after which the solvent was evaporated and the residue was purified by HPLC to give Mito₂-Metformin 1 (0.030 g, 25%).

$^{31}P$ NMR, (600.13): δ 21.61. $^1H$ NMR, (600.13 MHz): δ 7.93-7.73 (15H, m), 3.80-3.76 (2H, m), 3.38-3.34 (2H, m). $^{13}C$ NMR (75.47 MHz) A 158.3 (s), 158.1 (s), 135.1 (s), 133.7 (s), 133.6 (s), 130.3 (s), 131.2 (s), 117.6 (d, J=85), 35.1 (s), 20.6 (d, J=47). HRMS calculated for $C_{22}H_{25}N_5P$ $[C_{22}H_{25}N_5P]^+$ 390.1842, found 390.1842.

Example 7. Synthesis of Mito₆-Metformin (Mito-Met₆) 4

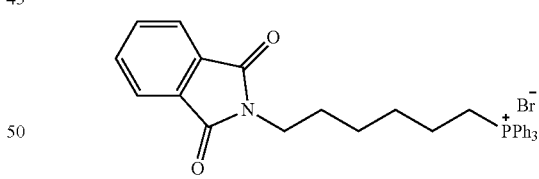

2

(6-phtalimidyl) triphenylphosphonium Bromide 2

A mixture containing Bromophtalimide (5 g, 0.016 mol) and triphenylphosphane (4.2 g, 0.019 mol) in acetonitrile (60 mL) was refluxed for 15 hours. The solvent distilled under reduced pressure. Purification of the crude product by flash chromatography on a silicagel ($CH_2Cl_2$/EtOH 80:20) afforded a white solid 2 (5.7 g, 62%).

$^{31}P$ NMR, (400.13): δ 24.38. $^1H$ NMR, (400.13 MHz): δ 7.90-7.66 (15H, m), 3.90-3.75 (2H, m), 3.65-3.55 (2H, m), 1.72-1.55 (6H, m), 1.40-1.28 (2H, m). $^{13}C$ NMR (75.47 MHz) δ 168.1 (s), 134.84 (s), 134.80 (s), 133.7 (s), 133.4 (s), 133.3 (s), 131.7 (s), 130.4 (s), 130.2 (s), 122.8 (s), 118.5 (s), 118.4 (s), 37.4 (s), 29.2 (d, J=16.5), 26.0 (s), 22.2 (d, J=4.4), 18.2 (s).

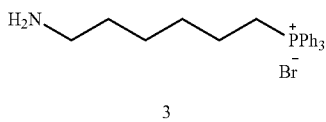

3

(6-Aminohexyl) triphenylphosphonium Bromide 3

To a solution of 2 (5.2 g, 0.009 mol) in EtOH (70 mL) was added 10 mL of hydrazine 1M in THF. The mixture was refluxed for 18 hours. The product was purified by flash chromatography on a silicagel ($CH_2Cl_2$/EtOH 80:20) afforded a yellow solid 3 (3 g, 75%).
$^{31}$P NMR, (400.13): δ 23.73. $^1$H NMR, (400.13 MHz): δ 7.90-7.66 (15H, m), 3.46-3.39 (2H, m), 2.91 (2H, t, J=7.5), 1.72-1.55 (6H, m), 1.40-1.28 (2H, m). $^{13}$C NMR (75.47 MHz) δ 136.4 (s), 136.3 (s), 134.9 (s), 134.8 (s), 133.0 (s), 131.7 (s), 131.6 (s), 130.9 (s), 127.0 (s), 120.4 (s), 119.6 (s), 40.8 (s), 31.2 (d, J=16.1), 29.0 (s), 26.9 (s), 23.5 (d, J=4.4), 23.0 (s), 22.5 (s).

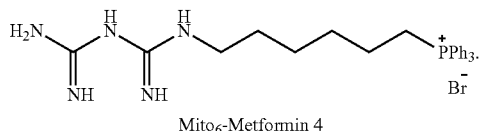

Mito$_6$-Metformin 4

A Mito-Met$_6$. A 1 g portion of (6-Aminohexyl) triphenylphosphonium Bromide (23 mmol) was dissolved in $CH_2Cl_2$ (15 mL) and the mixture was cooled to 0° C. A 4.53 mL portion of 1.0 M solution of HCl in diethyl ether (45 mmol) was added dropwise. After 90 min at room temperature, the solvent was removed under vacuum and dicyanamide (0.022 g, 0.26 mmol) was added. The neat mixture was heated at 180° C. for 2 h, the residue was dissolved in EtOH and purified by HPLC (C18 RP, $H_2O$/ACN gradient, 0.1% TFA) to give Mito-Metformin$_6$ (0.20 g, 17%). $^{31}$P NMR, (600.13): δ 24.6. $^1$H NMR, (600.13 MHz): δ 7.93-7.88 (3H, m), 7.81-7.77 (12H, m), 3.60-3.46 (2H, m), 3.05-3.00 (2H, m), 1.55-1.48 (2H, m), 1.48-1.42 (2H, m), 1.41-1.35 (2H, m), 1.31-1.24 (2H, m). $^{13}$C NMR (75.47 MHz) δ 158.2 (s), 157.9 (s), 134.9 (s), 133.6 (s), 133.5 (s), 130.3 (s), 130.2 (s), 118.2 (d, J=86), 40.0 (s), 30.0 (s), 29.5 (s), 25.9 (s), 22.2 (d, J=3), 20.5 (d, J=49). HRMS calculated for $C_{26}H_{33}N_5P$ $[C_{26}H_{33}N_5P]^+$ 446.2468, found 446.2467.

Example 8. Synthesis of Mito$_{10}$-Metformin 7

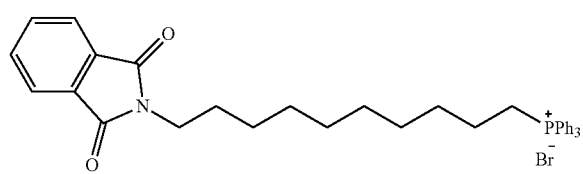

5

(10-phtalimidyl) triphenylphosphonium Bromide 5

A mixture containing Bromophtalimide (7 g, 0.019 mol) and triphenylphosphane (5 g, 0.019 mol) in acetonitrile (60 mL) was refluxed for 15 hours. The solvent distilled under reduced pressure. Purification of the crude product by flash chromatography on a silicagel ($CH_2Cl_2$/EtOH 80:20) afforded a white solid 5 (9 g, 73%). MS calculated for $[C_{36}H_{39}NO_2P]^+$, Br$^-$; $[C_{36}H_{39}NO_2P]^+$, 548.3, found: 548.3.

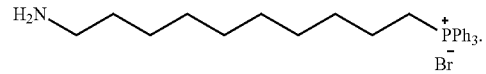

6

(10-Aminodecyl) triphenylphosphonium Bromide 6

To a solution of 5 (7 g, 0.0108 mol) in EtOH (70 mL) was added hydrazine (0.54 mL, 0.0108 mol). The mixture was refluxed for 15 hours. The solvent is distilled and the impurity was crystallized using a mixture $Et_2O$/EtOH (100 mL+45 mL). The product was purified by flash chromatography on a silicagel ($CH_2Cl_2$/EtOH 80:20) afforded a yellow solid 6 (4 g, 73%). $^{31}$P NMR (121.49 MHz) δ 24.61. $^1$H NMR (300.13 MHz) δ 7.95-7.73 (15H, m), 3.70-3.55 (2H, m), 2.80-2.70 (2H, m), 1.60-1.40 (6H, m), 1.35-1.10 (10H, m). MS calculated for $[C_{28}H_{37}NP]^+$, Br$^-$; $[C_{28}H_{37}NP]^+$, 418.2, found: 418.2.

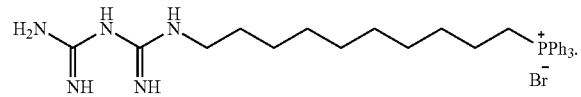

Mito$_{10}$-Metformin 7

Mito$_{10}$-metformin 7.

A 0.2 g portion of (10-Aminodecyl) triphenylphosphonium Bromide 2 (0.4 mmol) was dissolved in $CH_2Cl_2$ (3 mL) and the mixture was cooled to 0° C. A 500 μL portion of 1.0 M solution of HCl in diethyl ether (0.5 mmol) was added dropwise. After 1 h at room temperature, the solvent was removed under vacuum and dicyandiamide (0.034 g, 0.4 mmol) was added in BuOH (2 mL). The mixture was heated to reflux overnight, after which the solvent was evaporated and the residue was purified by HPLC to give Mito$_{10}$-Metformin 3 (0.060 g, 30%).
$^{31}$P NMR, (400.13): δ 23.77. $^1$H NMR, (400.13 MHz): δ 7.91-7.73 (15H, m), 3.42-3.33 (2H, m), 3.25-3.20 (2H, m), 1.69-1.51 (6H, m), 1.40-1.21 (10H, m). HRMS calculated for $C_{30}H_{41}N_5P$ $[C_{30}H_{41}N_5P]^+$ 502.3094, found 502.3094.

Example 9. Large Scale Synthesis of Mito-Met$_{10}$

A 2 g portion of (10-Aminodecyl) triphenylphosphonium bromide 2 (3.4 mmol) was dissolved in $CH_2Cl_2$ (15 mL) and the mixture was cooled to 0° C. A 4 mL portion of 1.0 M solution of HCl in diethyl ether (4 mmol) was added dropwise. After 1 h at room temperature, the solvent was removed under vacuum and dicyandiamide (0.34 g, 4 mmol) was added. The neat mixture was heated to 180° C. for 2 h., after which the residue was dissolved in EtOH and purified by HPLC (C18 RP, $H_2O$/ACN gradient, 0.1% TFA) to give Mito-Metformin$_{10}$ 3 (0.60 g, 28%). $^{31}$P NMR, (400.13): δ

23.77. $^1$H NMR, (400.13 MHz): δ 7.91-7.73 (15H, m), 3.42-3.33 (2H, m), 3.25-3.20 (2H, m), 1.69-1.51 (6H, m), 1.40-1.21 (10H, m). HRMS calculated for $C_{30}H_{41}N_5P$ $[C_{30}H_{41}N_5P]^+$ 502.3094, found 502.3094.

Example 10: Synthesis of Mito-Met$_{12}$

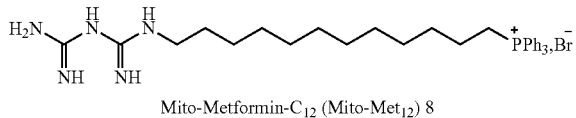

Mito-Metformin-C$_{12}$ (Mito-Met$_{12}$) 8

A 1 g portion of (12-Aminododecyl) triphenylphosphonium Bromide (1.9 mmol) was dissolved in CH$_2$Cl$_2$ (15 mL) and the mixture was cooled to 0° C. A 2 mL portion of 1.0 M solution of HCl in diethyl ether (2 mmol) was added dropwise. After 1 h at room temperature, the solvent was removed under vacuum and dicyandiamide (0.18 g, 2.1 mmol) was added. The neat mixture was heated to 180° C. for 2 h., after which the residue was dissolved in EtOH and purified by HPLC (C18 RP, H$_2$O/ACN gradient, 0.1% TFA) to give Mito-Metformin$_{12}$ 8 (0.30 g, 28%). $^{31}$P NMR, (400.13): δ 23.98. $^1$H NMR, (400.13 MHz): δ 7.94-7.73 (15H, m), 3.59-3.49 (2H, m), 3.17-3.07 (2H, m), 1.58-1.38 (6H, m), 1.32-1.12 (14H, m). HRMS calculated for $C_{32}H_{46}N_5P$ $[C_{30}H_{41}N_5P]^{++}$ 265.6740, found 265.6739.

Example 11. Ability to Target Modified Metformin to Specific Organelles

We demonstrated that a modified form of a well-tolerated anti-diabetic drug, metformin, can target specifically to mitochondria.

Although Metformin (FIG. 1) enters mitochondria, it does so rather inefficiently as a hydrophilic cation at physiological pH. We demonstrated that the addition of a positively-charged group (triphenyl phosphonium (TPP+)) to Met to produce a modified metformin analog (mitoMet) with an increased positive charge (FIG. 1). Novel Mito-Metformin analogs were created that are able to enter mitochondria 100-300 fold more efficacious than Metformin in cell culture and animal models of PD.

Example 12. Mito-Met Enhances Mitochondrial Respiration and Protects Against MPP+ and Rotenone-Induced Toxicity in N27 Dopaminergic Neuronal Cells The present technology demonstrates that modified metformin provides neuroprotective properties. Emerging studies have indicated that impaired mitochondrial biogenesis is associated with neurodegeneration and PD.

Figure 2B:
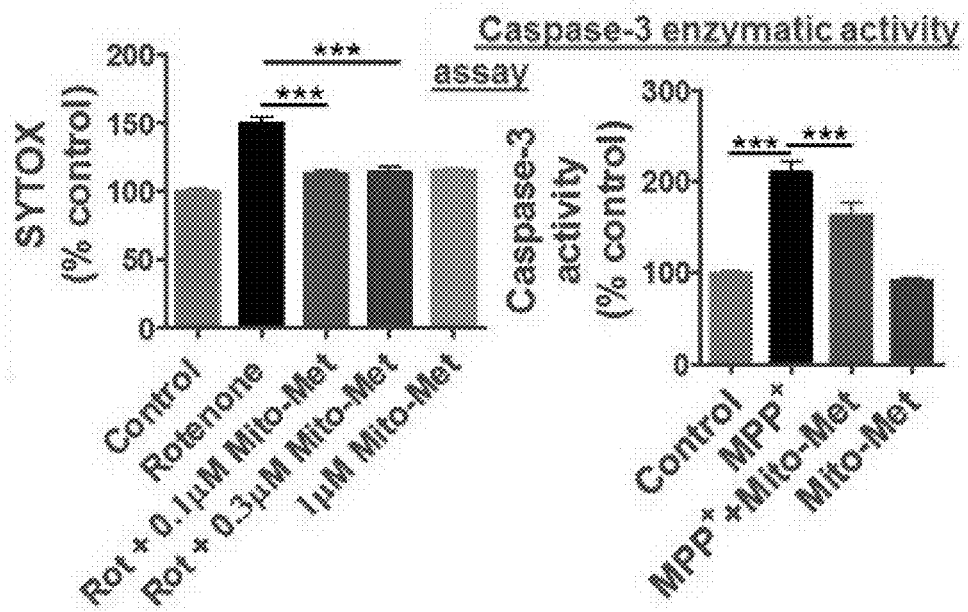

This example shows that pretreatment with a nanomolar concentration of mito-Met (100-300 nM) effectively protected N27 dopaminergic neuronal cells against the apoptotic cell death (measured by Sytox Green cytotoxicity (FIG. 2A) and caspase-3 activity (FIG. 2B)) induced by the Parkinsonian mitochondrial toxicant MPP$^+$ or rotenone, while mito-Met alone had no adverse effects (FIG. 2A-B). Furthermore, we observed that mito-Met itself, at both 1 and 10 μM, did not attenuate the activity of mitochondrial aconitase (FIG. 3A), whose inactivation is commonly used as a measure of mitochondrial oxidative damage (Cantu et al., 2009), indicating that our novel compounds, mito-Met, do not adversely affect mitochondrial function.

Consistent with this finding, MitoSox staining assays revealed that mito-Met itself (0.1-1 μM) did not increase mitochondrial superoxide levels (FIG. 3B). In terms of pharmacological mechanisms of metformin, several in vitro studies reported that millimolar concentrations of the compound inhibit complex I in the mitochondrial respiratory chain (Carvalho et al., 2008; Owen et al., 2000). However, this notion is controversial since preservation of mitochondrial complex I activity has been reported in metformin-treated muscle cells (Vytla and Ochs, 2013), in livers of metformin-treated mice (Martin-Montalvo et al., 2013) and in skeletal muscles of metformin-treated humans (Larsen et al., 2012). Furthermore, the therapeutic dose of metformin in the plasma of metformin-treated humans (1000 mg/day orally) is approximately 0.1 mM (Bailey and Turner, 1996; Scheen, 1996), and at this concentration, metformin does not affect mitochondrial complex-1 activity. Thus, the recent reviews arguing against the proposed mechanism of direct inhibition of mitochondrial complex-1 by metformin are based on studies using supra-clinical doses of metformin to inhibit complex I. Given these conflicting results in the metformin literature, we wanted to determine whether our novel mito-Met formulation adversely affects mitochondrial function. We directly measured the effect of mito-Met on mitochondrial oxygen consumption rates (OCR) in N27 cells using a Seahorse extracellular flux analyzer (XF96). Our results indicate that 3-h incubation with nanomolar concentrations of mito-Met did not reduce, but rather significantly enhanced, both the basal and ATP-linked oxygen consumption (FIG. 4A-B), revealing highly beneficial properties of mito-Met on mitochondrial function. Also, cellular ATP content in N27 cells incubated with mito-Met was unaffected (FIG. 4C). Together, these results suggest that our mitochondria-targeted metformin analog (mito-Met) increases mitochondrial bioenergetic capacity and protects against dopaminergic neuronal cell death.

Example 13. Mito-Met Enhances AMPK/Akt/PKD1 Survival Signaling and Mitochondrial Biogenesis in N27 Dopaminergic Neuronal Cells In this example we assessed whether mito-Met alters mitochondrial biogenesis in a dopaminergic cell model. We treated N27 cells with varying doses of metformin or mito-Met for 24 h and examined AMPK activation by measuring phosphorylation of AMPK within its activation loop at T172. Consistent with previous results, treatment with 10-100 μM metformin significantly increased the phosphorylation of AMPK Thr172 (FIG. 5A). Interestingly, mito-Met induced AMPK activation of Thr172 phosphorylation at three orders of magnitude lower concentrations (10-300 nM), suggesting a higher efficiency of mitochondria-targeted metformin analog in activating the AMPK pathway.

In line with these findings, metformin, and more potently mito-Met at much lower concentrations upregulated protein levels of Tfam, a key activator of mitochondrial biogenesis (FIG. 5B). Additionally, exposure of N27 dopaminergic cells to 100 and 300 nM of mito-Met upregulated TFAM mRNA expression (FIG. 5C). In line with these results, mito-Met treatment also increased the mitochondrial DNA copy number in N27 cells (FIG. 5D). Moreover, we found that mito-Met rapidly (3-6 h) activated two major cell survival signaling pathways regulating neuronal survival, namely Akt and PKD1 (FIG. 5E). Collectively, these data suggest that mito-Met augments AMPK/Akt/PKD1 signaling activation and subsequent mitochondrial biogenesis in dopaminergic neuronal cells.

Example 14. Mito-Met Protects Against MPP$^+$-Induced Mitochondrial Fragmentation This Example demonstrates the protective effect of Mito-Met on cells by preventing mitochondrial fragmentation. We examined the effects of mito-Met on mitochondrial morphology and integrity in N27 dopaminergic cells exposed to the Parkinsonian toxin MPP$^+$. N27 cells were pretreated with 1 μM mito-Met for 6 h and then co-treated with 300 μM MPP$^+$ for 16 h. Mitochondria were visualized by staining with the cell-permeable mitochondrion-selective dye MitoTracker Red. As expected, MPP$^+$ induced considerable mitochondrial fragmentation as evident from loss of tubular and filamentous structure of mitochondria relative to untreated cells (Wang et al., 2011). In contrast, mito-Met substantially reduced MPP+-induced mitochondrial fragmentation (FIG. 6A). Of note, mito-Met alone had no influence on mitochondrial morphology. Quantitative analysis of mitochondrial length and circularity also confirmed a significant neuroprotective effect of mito-Met against mitochondrial injury (FIG. 6B).

Example 15. Mito-Met Protects Against MPP$^+$-Induced Toxicity in Primary Mesencephalic Cultures Mito-Met provides neuroprotection against dopaminergic cell death. This experiment demonstrates the neuroprotective effect of mito-Met against dopaminergic cell death by testing the ability of Mito-Met to protect primary dopaminergic neurons from MPP$^+$-induced neurodegeneration.

Primary mesencephalic neuronal cultures were treated for 24 h with 10 μM MPP$^+$ alone or co-treated with 100 and 300 nM mito-Met, dopaminergic neurotoxicity was assessed by TH immunocytochemistry (FIG. 7A) and quantification of neurite length of TH$^+$ neurons (FIG. 7B). MPP$^+$ reduced the neurite length of TH-immunoreactive neurons to almost 45% of the vehicle-treated group, indicating significant dopaminergic neurotoxicity. Mito-Met co-treatments significantly (*, $p<0.05$ vs MPP+ alone) mitigated MPP$^+$-induced loss of TH neurite length.

Example 16. Mito-Met Improves Motor Behavior, Striatal Neurotransmitter Levels and Olfaction Dysfunction in a Mouse Model of Parkinson's Disease This example evaluated the neuroprotective efficacy of mito-Met in a genetic mouse model of mitochondrial dysfunction known as "MitoPark" mouse model. This model was developed in the laboratory of Nils-Göran Larsson at Karolinska Institute, Stockholm, Sweden by specific inactivation of Tfam in DA neurons of C57BL mice (Ekstrand et al., 2007). It recapitulates several features of PD in humans, such as adult-onset degeneration of nigrostriatal dopamine circuitry, progressive phenotypic manifestations and neurodegeneration, protein inclusions in nigral tissue, and motor deficits that are ameliorated by L-DOPA administration (Ekstrand et al., 2007; Galter et al., 2010). MitoPark mice exhibit progressively dopaminergic degeneration and motor deficits begin at around 12 weeks of age (Ekstrand and Galter, 2009; Ekstrand et al., 2007).

12-week-old C57BL/6 control and MitoPark mice were treated with 10 mg/kg mito-Met three times per week by oral lavage for eight weeks. Control mice received saline.

Figure 9A:
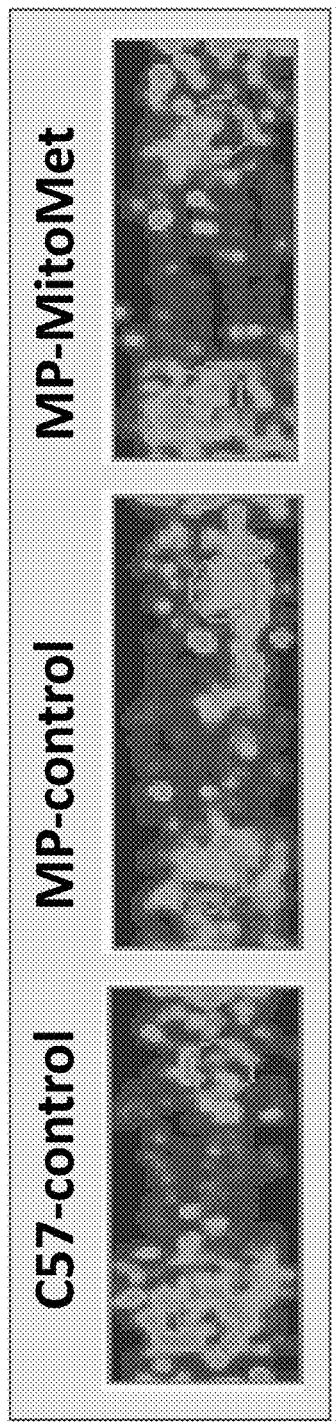
FIG. 9A-B demonstrates MitoPark mice display olfactory deficits attenuated by Mito-Met. During the social discrimination scent test, MitoPark mice did not show a significant preference for the foreign animals' bedding (of opposite sex) as opposed to the animal's own bedding as displayed in percent investigatory time being significantly less than in age matched control mice. MitoPark mice treated with Mito-Met had a higher investigatory time, meaning they preferred the novel bedding versus their own (FIG. 9B). *=p<0.05; **=p<0.01; MP=MitoPark.
Figure 9B:
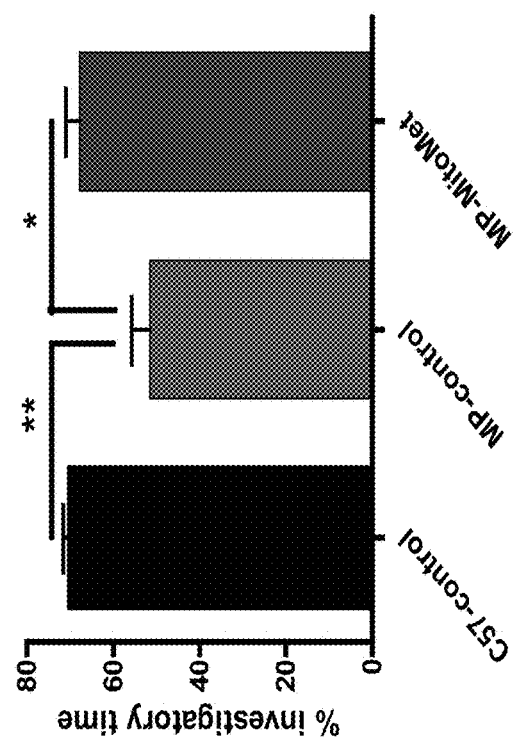

As shown in FIG. 8A-C, the locomotor activity plot and analysis of horizontal activity and total distance revealed severe motor deficits in MitoPark mice at 20 weeks of age, whereas the motor dysfunction was significantly recovered in mito-Met-treated MitoPark mice. Also, loss of the striatal neurotransmitter DA and its metabolites DAPAC were restored by mito-Met (FIG. 8D). Next, since growing evidence suggests that olfactory impairment is a characteristic and early feature of PD, preceding clinical motor symptoms by years, we assessed the protective effect of mito-Met against deficits in the sense of smell in MitoPark mice. Olfactory behavior was evaluated with a sniffing test, which measures the ability of the male mice to detect female pheromones. As shown in FIG. 9A-B, relative to C57BL/6 control mice, 16 week old MitoPark mice spent significantly less time sniffing female bedding, indicating an impaired olfaction in these mice. Notably, the impairment of olfaction was markedly improved by mito-Met treatment. All these results strongly suggest in vivo protective effects of mito-Met.

The experimental evidence provide herein shows that a modified mitochondria-targeted metformin, when compared to metformin, provides enhanced neurobehavioral and neuroprotective benefits against mitochondrial defect-linked neurodegenerative processes, such as those found in PD, by improving brain mitochondrial efficiency and by activating mitochondrial biogenesis signaling pathway.

REFERENCES

Akahoshi, E., et al., 2009. Effect of dioxins on regulation of tyrosine hydroxylase gene expression by aryl hydrocarbon receptor: a neurotoxicology study. Environ Health. 8, 24.

Asaithambi, A., et al., 2014. Protein kinase D1 (PKD1) phosphorylation promotes dopaminergic neuronal survival during 6-OHDA-induced oxidative stress. PLoS One. 9, e96947.

Asaithambi, A., et al., 2011. Protein kinase D1 (PKD1) activation mediates a compensatory protective response during early stages of oxidative stress-induced neuronal degeneration. Mol Neurodegener. 6, 43.

Ay, M., et al., 2015. Molecular Cloning, Epigenetic Regulation and Functional Characterization of Prkd1 Gene Promoter in Dopaminergic Cell Culture Models of Parkinson's Disease. J Neurochem.

Bailey, C. J., Turner, R. C., 1996. Metformin. N Engl J Med. 334, 574-9.

Beal, M. F., 2003. Mitochondria, oxidative damage, and inflammation in Parkinson's disease. Ann N Y Acad Sci. 991, 120-31.

Bergheim, I., et al., 2006. Metformin prevents endotoxin-induced liver injury after partial hepatectomy. J Pharmacol Exp Ther. 316, 1053-61.

Bortolozzi, A. A., et al., 2004. Effects of 2,4-dichlorophenoxyacetic acid exposure on dopamine D2-like receptors in rat brain. Neurotoxicol Teratol. 26, 599-605.

Brighina, L., et al., 2008. Alpha-synuclein, pesticides, and Parkinson disease: a case-control study. Neurology. 70, 1461-9.

Cantu, D., et al., 2009. Oxidative inactivation of mitochondrial aconitase results in iron and H2O2-mediated neurotoxicity in rat primary mesencephalic cultures. PLoS One. 4, e7095.

Carvalho, C., et al., 2008. Metformin promotes isolated rat liver mitochondria impairment. Mol Cell Biochem. 308, 75-83.

Cecil, P. F., Sr., Young, A. L., 2008. Operation FLYSWATTER: a war within a war. Environ Sci Pollut Res Int. 15, 3-7.

Cereda, E., et al., 2013. Diabetes and risk of Parkinson's disease. Mov Disord. 28, 257.

Chaturvedi, R. K., Flint Beal, M., 2013. Mitochondrial diseases of the brain. Free Radic Biol Med. 63, 1-29.

Chen, H., et al., 2008. Peripheral inflammatory biomarkers and risk of Parkinson's disease. Am J Epidemiol. 167, 90-5.

Choi, J. S., et al., 2010. AMP-activated protein kinase is activated in Parkinson's disease models mediated by 1-methyl-4-phenyl-1,2,3,6-tetrahydropyridine. Biochem Biophys Res Commun. 391, 147-51.

Ciron, C., et al., 2015. PGC-1alpha activity in nigral dopamine neurons determines vulnerability to alpha-synuclein. Acta Neuropathol Commun. 3, 16.

Cranmer, M., et al., 2000. Exposure to 2,3,7,8-tetrachlorodibenzo-p-dioxin (TCDD) is associated with hyperinsulinemia and insulin resistance. Toxicol Sci. 56, 431-6.

Dardiotis, E., et al., 2013. The interplay between environmental and genetic factors in Parkinson's disease susceptibility: the evidence for pesticides. Toxicology. 307, 17-23.

Dominy, J. E., Puigserver, P., 2013. Mitochondrial biogenesis through activation of nuclear signaling proteins. Cold Spring Harb Perspect Biol. 5.

Dunn, C. J., Peters, D. H., 1995. Metformin. A review of its pharmacological properties and therapeutic use in non-insulin-dependent diabetes mellitus. Drugs. 49, 721-49.

Ekstrand, M. I., Galter, D., 2009. The MitoPark Mouse—an animal model of Parkinson's disease with impaired respiratory chain function in dopamine neurons. Parkinsonism Relat Disord. 15 Suppl 3, S185-8.

Ekstrand, M. I., et al., 2007. Progressive parkinsonism in mice with respiratory-chain-deficient dopamine neurons. Proc Natl Acad Sci USA. 104, 1325-30.

Exner, N., et al., 2012. Mitochondrial dysfunction in Parkinson's disease: molecular mechanisms and pathophysiological consequences. EMBO J. 31, 3038-62.

Feng, J., 2006. Microtubule: a common target for parkin and Parkinson's disease toxins. Neuroscientist. 12, 469-76.

Ferrer, I., et al., 2012. Neurochemistry and the non-motor aspects of PD. Neurobiol Dis. 46, 508-26.

Galter, D., et al., 2010. MitoPark mice mirror the slow progression of key symptoms and L-DOPA response in Parkinson's disease. Genes Brain Behav. 9, 173-81.

Ghosh, A., et al., 2010. Neuroprotection by a mitochondria-targeted drug in a Parkinson's disease model. Free Radic Biol Med. 49, 1674-84.

Ghosh, A., et al., 2012. Anti-inflammatory and neuroprotective effects of an orally active apocynin derivative in pre-clinical models of Parkinson's disease. J Neuroinflammation. 9, 241.

Ghosh, A., et al., 2013. The peptidyl-prolyl isomerase Pin1 up-regulation and proapoptotic function in dopaminergic neurons: relevance to the pathogenesis of Parkinson disease. J Biol Chem. 288, 21955-71.

Gongol, B., et al., 2013. AMPKalpha2 exerts its anti-inflammatory effects through PARP-1 and Bcl-6. Proc Natl Acad Sci USA. 110, 3161-6.

Gordon, R., et al., 2012. Proteolytic activation of proapoptotic kinase protein kinase Cdelta by tumor necrosis factor alpha death receptor signaling in dopaminergic neurons during neuroinflammation. J Neuroinflammation. 9, 82.

Grahame Hardie, D., 2014. AMP-activated protein kinase: a key regulator of energy balance with many roles in human disease. J Intern Med.

Hakansson, A., et al., 2005. Interaction of polymorphisms in the genes encoding interleukin-6 and estrogen receptor beta on the susceptibility to Parkinson's disease. Am J Med Genet B Neuropsychiatr Genet. 133B, 88-92.

Haley, N. J., et al., 2014. Detection of chronic wasting disease in the lymph nodes of free-ranging cervids by real-time quaking-induced conversion. J Clin Microbiol. 52, 3237-43.

Hancock, D. B., et al., 2008. Pesticide exposure and risk of Parkinson's disease: a family-based case-control study. BMC Neurol. 8, 6.

Henderson, D. M., et al., 2015. Quantitative assessment of prion infectivity in tissues and body fluids by real-time quaking-induced conversion. J Gen Virol. 96, 210-9.

Hirsch, E. C., Hunot, S., 2009. Neuroinflammation in Parkinson's disease: a target for neuroprotection? Lancet Neurol. 8, 382-97.

Jager, S., et al., 2007. AMP-activated protein kinase (AMPK) action in skeletal muscle via direct phosphorylation of PGC-1alpha. Proc Natl Acad Sci USA. 104, 12017-22.

Kajbaf, F., et al., 2015. Therapeutic Concentrations of Metformin: A Systematic Review. Clin Pharmacokinet.

Kalariya, N. M., et al., 2012. Antidiabetic drug metformin suppresses endotoxin-induced uveitis in rats. Invest Ophthalmol Vis Sci. 53, 3431-40.

Kargul, J., et al., 2015. Mitochondrial diseases: From the lab bench to therapies. Int J Biochem Cell Biol. 63, 1.

Keogh, M. J., Chinnery, P. F., 2015. Mitochondrial DNA mutations in neurodegeneration. Biochim Biophys Acta.

Kowal, S. L., et al., 2013. The current and projected economic burden of Parkinson's disease in the United States. Mov Disord. 28, 311-8.

Kruger, R., et al., 2000. Genetic analysis of immunomodulating factors in sporadic Parkinson's disease. J Neural Transm. 107, 553-62.

Laino, C., 2005. Military deployment may raise risk of Parkinson disease. Neurology Today. 5, 48.

Larsen, S., et al., 2012. Metformin-treated patients with type 2 diabetes have normal mitochondrial complex I respiration. Diabetologia. 55, 443-9.

Lopert, P., et al., 2012. Thioredoxin reductase deficiency potentiates oxidative stress, mitochondrial dysfunction and cell death in dopaminergic cells. PLoS One. 7, e50683.

Martin-Montalvo, A., et al., 2013. Metformin improves healthspan and lifespan in mice. Nat Commun. 4, 2192.

Maruthur, N. M., et al., 2014. The pharmacogenetics of type 2 diabetes: a systematic review. Diabetes Care. 37, 876-86.

McClean, P. L., et al., 2011. The diabetes drug liraglutide prevents degenerative processes in a mouse model of Alzheimer's disease. J Neurosci. 31, 6587-94.

McGeer, P. L., et al., 2002. Association of interleukin-1 beta polymorphisms with idiopathic Parkinson's disease. Neurosci Lett. 326, 67-9.

Moon, H. E., Paek, S. H., 2015. Mitochondrial Dysfunction in Parkinson's Disease. Exp Neurobiol. 24, 103-16.

Mudo, G., et al., 2012. Transgenic expression and activation of PGC-1alpha protect dopaminergic neurons in the MPTP mouse model of Parkinson's disease. Cell Mol Life Sci. 69, 1153-65.

Ng, C. H., et al., 2012. AMP kinase activation mitigates dopaminergic dysfunction and mitochondrial abnormalities in Drosophila models of Parkinson's disease. J Neurosci. 32, 14311-7.

Ngwa, H. A., et al., 2013. Vanadium exposure induces olfactory dysfunction in an animal model of metal neurotoxicity. Neurotoxicology.

O'Donnell, K. C., et al., 2014. Axon degeneration and PGC-1alpha-mediated protection in a zebrafish model of alpha-synuclein toxicity. Dis Model Mech. 7, 571-82.

Orru, C. D., et al., 2014. A test for Creutzfeldt-Jakob disease using nasal brushings. N Engl J Med. 371, 519-29.

Orru, C. D., et al., 2015. Rapid and sensitive RT-QuIC detection of human Creutzfeldt-Jakob disease using cerebrospinal fluid. MBio. 6.

Orru, C. D., et al., 2012. New generation QuIC assays for prion seeding activity. Prion. 6, 147-52.

Owen, M. R., et al., 2000. Evidence that metformin exerts its anti-diabetic effects through inhibition of complex 1 of the mitochondrial respiratory chain. Biochem J. 348 Pt 3, 607-14.

Pacelli, C., et al., 2011. Mitochondrial defect and PGC-1alpha dysfunction in parkin-associated familial Parkinson's disease. Biochim Biophys Acta. 1812, 1041-53.

Patil, S. P., et al., 2014. Neuroprotective effect of metformin in MPTP-induced Parkinson's disease in mice. Neuroscience. 277, 747-54.

Przedborski, S., 2010. Inflammation and Parkinson's disease pathogenesis. Mov Disord. 25 Suppl 1, S55-7.

Reagan-Shaw, S., et al., 2008. Dose translation from animal to human studies revisited. FASEB J. 22, 659-61.

Rena, G., et al., 2013. Molecular mechanism of action of metformin: old or new insights? Diabetologia. 56, 1898-906.

Roman, E. A., et al., 2010. Central leptin action improves skeletal muscle AKT, AMPK, and PGC1 alpha activation by hypothalamic PI3K-dependent mechanism. Mol Cell Endocrinol. 314, 62-9.

Rose, M. R., Brix, K. A., 2006. Neurological disorders in Gulf War veterans. Philos Trans R Soc Lond B Biol Sci. 361, 605-18.

Ryan, B. J., et al., 2015. Mitochondrial dysfunction and mitophagy in Parkinson's: from familial to sporadic disease. Trends Biochem Sci. 40, 200-10.

Sanders, L. H., Greenamyre, J. T., 2013. Oxidative damage to macromolecules in human Parkinson disease and the rotenone model. Free Radic Biol Med. 62, 111-20.

Santiago, J. A., Potashkin, J. A., 2013. Shared dysregulated pathways lead to Parkinson's disease and diabetes. Trends Mol Med. 19, 176-86.

Scarpulla, R. C., et al., 2012. Transcriptional integration of mitochondrial biogenesis. Trends Endocrinol Metab. 23, 459-66.

Schapira, A. H., 2012. Mitochondrial diseases. Lancet. 379, 1825-34.

Schapira, A. H., Jenner, P., 2011. Etiology and pathogenesis of Parkinson's disease. Mov Disord. 26, 1049-55.

Scheen, A. J., 1996. Clinical pharmacokinetics of metformin. Clin Pharmacokinet. 30, 359-71.

Schwab, C., et al., 2010. Inflammation in transgenic mouse models of neurodegenerative disorders. Biochim Biophys Acta. 1802, 889-902.

Shi, S., et al., 2015. Quantitative Real-Time Quaking-Induced Conversion Allows Monitoring of Disease-Modifying Therapy in the Urine of Prion-Infected Mice. J Neuropathol Exp Neurol.

Shin, J. H., et al., 2011. PARIS (ZNF746) repression of PGC-1alpha contributes to neurodegeneration in Parkinson's disease. Cell. 144, 689-702.

Sprenger, F., Poewe, W., 2013. Management of motor and non-motor symptoms in Parkinson's disease. CNS Drugs. 27, 259-72.

Steinberg, G. R., Kemp, B. E., 2009. AMPK in Health and Disease. Physiol Rev. 89, 1025-78.

Subramaniam, S. R., Chesselet, M. F., 2013. Mitochondrial dysfunction and oxidative stress in Parkinson's disease. Prog Neurobiol. 106-107, 17-32.

Sun, F., et al., 2006. Proteasome inhibitor MG-132 induces dopaminergic degeneration in cell culture and animal models. Neurotoxicology. 27, 807-15.

Sun, Y., et al., 2012. Risk of Parkinson disease onset in patients with diabetes: a 9-year population-based cohort study with age and sex stratifications. Diabetes Care. 35, 1047-9.

Tanner, C. M., et al., 2014. The disease intersection of susceptibility and exposure: chemical exposures and neurodegenerative disease risk. Alzheimers Dement. 10, S213-25.

Tanner, C. M., et al., 2011. Rotenone, paraquat, and Parkinson's disease. Environ Health Perspect. 119, 866-72.

Taylor, T. N., et al., 2010. Behavioral phenotyping of mouse models of Parkinson's disease. Behav Brain Res. 211, 1-10.

Thomas, R. R., et al., 2012. Impaired complex-I mitochondrial biogenesis in Parkinson disease frontal cortex. J Parkinsons Dis. 2, 67-76.

Trinh, J., Farrer, M., 2013. Advances in the genetics of Parkinson disease. Nat Rev Neurol. 9, 445-54.

Tsunemi, T., La Spada, A. R., 2012. PGC-1alpha at the intersection of bioenergetics regulation and neuron function: from Huntington's disease to Parkinson's disease and beyond. Prog Neurobiol. 97, 142-51.

Valero, T., 2014. Mitochondrial biogenesis: pharmacological approaches. Curr Pharm Des. 20, 5507-9.

Villena, J. A., 2015. New insights into PGC-1 coactivators: redefining their role in the regulation of mitochondrial function and beyond. FEBS J. 282, 647-72.

Viollet, B., et al., 2012. Cellular and molecular mechanisms of metformin: an overview. Clin Sci (Lond). 122, 253-70.

Vytla, V. S., Ochs, R. S., 2013. Metformin increases mitochondrial energy formation in L6 muscle cell cultures. J Biol Chem. 288, 20369-77.

Wahlqvist, M. L., et al., 2012. Metformin-inclusive sulfonylurea therapy reduces the risk of Parkinson's disease occurring with Type 2 diabetes in a Taiwanese population cohort. Parkinsonism Relat Disord. 18, 753-8.

Wahner, A. D., et al., 2007. Inflammatory cytokine gene polymorphisms and increased risk of Parkinson disease. Arch Neurol. 64, 836-40.

Wang, L., et al., 2014. Metabolic inflammation exacerbates dopaminergic neuronal degeneration in response to acute MPTP challenge in type 2 diabetes mice. Exp Neurol. 251, 22-9.

Wang, X., et al., 2011. DLP1-dependent mitochondrial fragmentation mediates 1-methyl-4-phenylpyridinium toxicity in neurons: implications for Parkinson's disease. Aging Cell. 10, 807-23.

Wu, Y. R., et al., 2007. Tumor necrosis factor-alpha promoter polymorphism is associated with the risk of Parkinson's disease. Am J Med Genet B Neuropsychiatr Genet. 144B, 300-4.

Xie, Z., et al., 2011. Improvement of cardiac functions by chronic metformin treatment is associated with enhanced cardiac autophagy in diabetic OVE26 mice. Diabetes. 60, 1770-8.

Xu, Q., et al., 2011. Diabetes and risk of Parkinson's disease. Diabetes Care. 34, 910-5.

Yan, J., et al., 2014. Inflammatory response in Parkinson's disease (Review). Mol Med Rep. 10, 2223-33.

Young, A. L., Cecil, P. F., Sr., 2011. Agent Orange exposure and attributed health effects in Vietnam veterans. Mil Med. 176, 29-34.

Zaheer, F., Slevin, J. T., 2011. Trichloroethylene and Parkinson disease. Neurol Clin. 29, 657-65.

Zhang, D., et al., 2007. Neuroprotective effect of protein kinase C delta inhibitor rottlerin in cell culture and animal models of Parkinson's disease. J Pharmacol Exp Ther. 322, 913-22.

Zheng, B., et al., 2010. PGC-1alpha, a potential therapeutic target for early intervention in Parkinson's disease. Sci Transl Med. 2, 52ra73.

We claim:

1. A method for providing a subject in need thereof with neuroprotection, comprising administering to said subject a neuroprotective composition which includes an effective amount of the mito-metformin compound of the following structure,

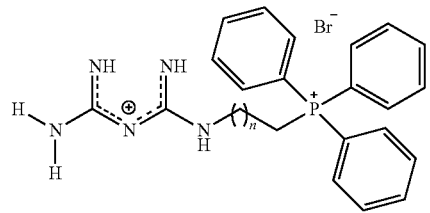

wherein n is selected from the group consisting of one (1), five (5), nine (9), and eleven (11).

2. The method of claim 1, wherein the subject suffers from a neurodegenerative disease.

3. The method of claim 2, wherein the subject suffers from a neurodegenerative disease selected from the group consisting of Parkinson's disease, Alzheimer's disease and other related neurological diseases.

4. The method of claim 1, wherein the subject is a mammal.

5. The method of claim 4, wherein the mammal is a human.

6. The method of claim 1, wherein the administering to said subject the neuroprotective composition prevents, reduces or reverses neuronal cell death within the subject.

7. The method of claim 1, wherein the method treats a neural injury in a subject having a neurodegenerative disease by administering an effective amount of the neuroprotection composition in order to treat the neural injury.

8. The method of claim 1, wherein the neuroprotective composition is administered in an amount effective to prevent, reduce or treat at least one symptom in a subject suffering from a neurodegenerative disease.

9. The method of claim 8, wherein the neurodegenerative disease is Parkinson's disease or Alzheimer's disease.

* * * * *

UNITED STATES PATENT AND TRADEMARK OFFICE
CERTIFICATE OF CORRECTION

Page 1 of 1

PATENT NO. : 9,956,233 B2
APPLICATION NO. : 15/294083
DATED : May 1, 2018
INVENTOR(S) : Anumantha Kanthasamy It is certified that error appears in the above-identified patent and that said Letters Patent is hereby corrected as shown below:

In the Specification

Column 18, Line 36 - "A" should be -- $\lambda$ --

Signed and Sealed this
Sixteenth Day of July, 2019

Andrei Iancu
*Director of the United States Patent and Trademark Office*